(12) United States Patent
Cooper

(10) Patent No.: US 10,591,476 B1
(45) Date of Patent: *Mar. 17, 2020

(54) SERIALLY DEPOSITED BIOMOLECULES

(71) Applicant: CUSTOMARRAY, INC., Bothwell, WA (US)

(72) Inventor: John Cooper, Seattle, WA (US)

(73) Assignee: CustomArray, Inc., Bothwell, WA (US)

( * ) Notice: Subject to any disclaimer, the term of this patent is extended or adjusted under 35 U.S.C. 154(b) by 109 days.

This patent is subject to a terminal disclaimer.

(21) Appl. No.: 15/936,298

(22) Filed: Mar. 26, 2018

Related U.S. Application Data

(63) Continuation of application No. 12/930,977, filed on Jan. 20, 2011, now Pat. No. 9,927,434.

(60) Provisional application No. 61/336,386, filed on Jan. 20, 2010.

(51) Int. Cl.
*G01N 33/53* (2006.01)
*G01N 33/543* (2006.01)

(52) U.S. Cl.
CPC .............................. *G01N 33/5438* (2013.01)

(58) Field of Classification Search
None
See application file for complete search history.

(56) References Cited

U.S. PATENT DOCUMENTS

| | | | |
|---|---|---|---|
| 3,720,591 A | 3/1973 | Skarlos | |
| 3,950,357 A | 4/1976 | Kahan | |
| 4,165,320 A | 8/1979 | Ondetti | |
| 4,563,263 A | 1/1986 | Oyama | |
| 4,840,893 A | 6/1989 | Hill | |
| 5,143,854 A | 9/1992 | Pirrung | |
| 5,445,934 A | 8/1995 | Fodor | |
| 5,510,270 A | 4/1996 | Fodor | |
| 5,540,828 A | 7/1996 | Yacynych | |
| 5,653,939 A | 8/1997 | Hollis | |
| 5,667,667 A | 9/1997 | Southern | |

(Continued)

FOREIGN PATENT DOCUMENTS

| | | |
|---|---|---|
| EP | 1420252 | 5/2004 |
| JP | 2005166601 | 6/2006 |

(Continued)

OTHER PUBLICATIONS

ISR, Application No. 05849631.6 PCT/US2005/041906, dated May 24, 2007, 4 pages.

(Continued)

*Primary Examiner* — Robert T. Crow
(74) *Attorney, Agent, or Firm* — Sci-Law Strategies, PC

(57) ABSTRACT

Disclosed herein is a multiplex microarray having serially attached non-functionalized biomolecules attached to a polymer coating covering each electrode of an array of electrodes for assays and a method of making the multiplex microarray. The method comprises serially blocking the electrodes of the microarray with a blocking protein, electropolymerizing pyrrole or a functionalized pyrrole on the electrodes where the biomolecule is not present during polymerization, exposing the microarray to a biomolecular solution containing a non-functionalized biomolecule for attachment to the polymer coating, and then repeating the steps to form the multiplex microarray.

20 Claims, 23 Drawing Sheets

Specification includes a Sequence Listing.

(56) References Cited

U.S. PATENT DOCUMENTS

| | | | |
|---|---|---|---|
| 5,695,940 A | 12/1997 | Drmanac | |
| 5,723,344 A | 3/1998 | Malibat | |
| 5,766,550 A | 6/1998 | Kaplan | |
| 5,824,473 A | 10/1998 | Meade | |
| 5,874,047 A | 2/1999 | Schoning | |
| 5,912,339 A | 6/1999 | Miller | |
| 5,928,905 A | 7/1999 | Stemmer | |
| 5,929,208 A | 7/1999 | Heller | |
| 5,953,681 A | 9/1999 | Cantatore | |
| 6,013,440 A | 1/2000 | Lipshutz | |
| 6,017,696 A | 1/2000 | Heller | |
| 6,051,380 A | 4/2000 | Sosnowski | |
| 6,066,448 A | 5/2000 | Wohlstader | |
| 6,093,302 A | 7/2000 | Montgomery | |
| 6,197,881 B1 * | 3/2001 | Cosnier | C12N 11/02 435/177 |
| 6,280,595 B1 | 8/2001 | Montgomery | |
| 6,320,041 B1 | 11/2001 | Hogrefe | |
| 6,391,558 B1 | 5/2002 | Henkens | |
| 6,444,111 B1 | 9/2002 | Montgomery | |
| 6,456,942 B1 | 9/2002 | Anderson | |
| 6,475,699 B2 | 11/2002 | Uetani | |
| 6,518,024 B2 | 2/2003 | Choong | |
| 6,576,426 B2 | 6/2003 | Southern | |
| 6,586,211 B1 | 7/2003 | Stahler | |
| 6,683,446 B1 * | 1/2004 | Pope | B01J 19/0046 205/81 |
| 6,743,564 B2 | 6/2004 | Hatakeyama | |
| 6,780,582 B1 | 8/2004 | Wagner | |
| 6,824,669 B1 | 11/2004 | Li | |
| 6,921,636 B1 | 7/2005 | Brennan | |
| 6,960,298 B2 | 11/2005 | Krotz | |
| 7,008,769 B2 | 3/2006 | Henderson | |
| 7,541,314 B2 | 6/2009 | Suciu | |
| 7,557,069 B2 | 7/2009 | Strathmann | |
| 8,855,955 B2 | 10/2014 | Peyvan | |
| 9,267,213 B1 | 2/2016 | Maurer | |
| 9,339,782 B1 | 5/2016 | Gindilis | |
| 9,394,167 B2 | 7/2016 | Maurer | |
| 9,927,434 B2 * | 3/2018 | Cooper | G01N 33/5438 |
| 9,983,204 B2 | 5/2018 | Maurer | |
| 10,006,131 B1 | 6/2018 | Maurer | |
| 10,261,075 B2 | 4/2019 | Maurer | |
| 10,286,377 B1 | 5/2019 | Gindilis | |
| 2001/0053529 A1 | 12/2001 | Gindilis | |
| 2002/0090738 A1 | 7/2002 | Cozzette | |
| 2002/0172963 A1 | 11/2002 | Kelley | |
| 2003/0022150 A1 | 1/2003 | Sampson | |
| 2003/0050437 A1 | 3/2003 | Montgomery | |
| 2003/0077515 A1 * | 4/2003 | Chen | B82Y 30/00 429/231.8 |
| 2003/0111356 A1 | 6/2003 | Strathmann | |
| 2003/0113713 A1 | 6/2003 | Glezer | |
| 2003/0134989 A1 | 7/2003 | Aldrich | |
| 2003/0152919 A1 | 8/2003 | Roelens | |
| 2003/0186226 A1 | 10/2003 | Brennan | |
| 2003/0190632 A1 | 10/2003 | Sosnowski | |
| 2003/0194709 A1 | 10/2003 | Yang | |
| 2004/0073017 A1 | 4/2004 | Skrzypcznski | |
| 2004/0238369 A1 | 12/2004 | Southern | |
| 2005/0008860 A1 * | 1/2005 | Garnier | C08G 61/124 428/403 |
| 2005/0043894 A1 | 2/2005 | Fernandez | |
| 2005/0212902 A1 | 9/2005 | Cook | |
| 2005/0239112 A1 | 10/2005 | Padmanabhan | |
| 2005/0272088 A1 | 12/2005 | Cook | |
| 2006/0035218 A1 | 2/2006 | Oleinikov | |
| 2006/0102471 A1 | 5/2006 | Adermann | |
| 2006/0105355 A1 | 5/2006 | Maurer | |
| 2006/0160100 A1 | 7/2006 | Gao | |
| 2006/0231411 A1 | 10/2006 | Maurer | |
| 2007/0034513 A1 | 2/2007 | Maurer | |
| 2007/0065877 A1 | 3/2007 | Maurer | |
| 2007/0072169 A1 | 3/2007 | Peyvan | |
| 2007/0231794 A1 | 10/2007 | Dill | |
| 2007/0292855 A1 | 12/2007 | Dubin | |
| 2008/0035494 A1 | 2/2008 | Gomez | |
| 2008/0039342 A1 | 2/2008 | Tian | |
| 2008/0125327 A1 | 5/2008 | Kumar | |
| 2009/0280998 A1 | 11/2009 | Maurer | |
| 2010/0276734 A1 * | 11/2010 | Josowicz | G01N 27/3277 257/253 |
| 2011/0281766 A1 | 11/2011 | Cooper | |
| 2016/0354751 A1 | 12/2016 | Maurer | |

FOREIGN PATENT DOCUMENTS

| | | | |
|---|---|---|---|
| WO | WO9603417 | 2/1996 | |
| WO | WO0051721 | 9/2000 | |
| WO | WO0123082 | 4/2001 | |
| WO | WO0231463 | 4/2002 | |
| WO | WO0231481 | 4/2002 | |
| WO | WO02090963 | 11/2002 | |
| WO | WO02103061 | 12/2002 | |
| WO | WO03020415 | 3/2003 | |
| WO | WO04024886 | 3/2004 | |
| WO | WO2006055810 | 5/2006 | |
| WO | WO 2008/073157 A2 * | 6/2008 | C12M 1/40 |

OTHER PUBLICATIONS

Extended European Search Report, Application No. 05849631.6 PCT/US2005/041906, dated Sep. 23, 2010, 9 pages.

Office Action, Application No. 05849631.6 PCT/US2005/041906, dated May 2, 2012, 3 pages.

Rule 71(3) EPC European Communication, Application No. 05849631.6 PCT/US2005/041906, dated Jul. 23, 2018, 11 pages.

Article 94(3) European Communication, Application No. 05849631.6 PCT/US2005/041906, dated Nov. 25, 2015, 5 pages.

Extended European Search Report, Application No. 06739757.0 PCT/US2006/011150, dated Jan. 20, 2011, 9 pages.

Communication from the examining division, Application No. 06739757.0 PCT/US2006/011150, dated Dec. 11, 2015, 29 pages.

European Search Report, Application No. EP06750351.6 PCT/US2006/014288 dated Dec. 2, 2010, 9 pages.

Office Action, Application No. 06750351.6 PCT/US2006/014288 dated Feb. 21, 2013, 4 pages.

Article 116(1) European Communication, Application No. 06750351.6 PCT/US2006/014288, dated Nov. 24, 2015, 9 pages.

Afshari et al., "Application of Complementary DNA Microarray Technology to Carcinogen Identification . . . ", Cancer Res., 1999, pp. 4759-4760, vol. 59.

Bard et al., "Azo, Azoxy and Diazo Compounds," Encyclo. Of Electrochemistry of the Elements, 1979, pp. 179-209, vol. XIII-4, NY, NY.

Bakker E (2004) Electrochemical sensors. Anal Chem 76: 3285-3298.

Batchelor-McAuley, C.; Wildgoose, G. G.; Compton, R. G. The physicochemical aspects of DNA sensing using electrochemical methods. Biosens. Bioelectron. 2009, 24, 3183-3190.

Beier et al., "Versatile Derivatisation of Solid Support Media for Convalent Bonding . . . " Nucleic Acids Research, 1999, pp. 1970-1977, vol. 27, No. 9.

Caillat, P.; David, D.; Belleville, M.; Clerc, F.; Massit, C.; Revol-Cavalier, F.; Peltie, P.; Livache, T.; Bidan, G.; Roget, A.; Crapez, E. Biochips on CMOS: An active matrix address array for DNA analysis. Sens. Actuat. B: Chem. 1999, 61, 154-162.

Cahill and Nordhoff, "Protein Arrays & Their Role in Protemics" Adv. Biochem. Engin/Biotechnol., 2003, pp. 177-187, vol. 83.

Campbell et al., "Enzyme-Amplified Amperometric Sandwich Test for RNA and DNA" Anal. Chem., 2002, 158-162, 74(1) American Chemical Society.

Chen, C.; Nagy, G.; Walker, A. V.; Maurer, K.; McShea, A.; Moeller, K. D. Building addressable libraries: The use of a mass spectrometry cleavable linker for monitoring reactions on a microelectrode array. J. Am. Chem. Soc. 2006, 128, 16020-16021.

Cosnier S (1999) Biomolecule immobilization on electrode surfaces by entrapment or attachment to electrochemically polymerized films. A review. Biosensors & Bioelectronics 14: 443-456.

(56) References Cited

OTHER PUBLICATIONS

Cuzin, M. DNA chips: A new tool for genetic analysis and diagnostics. Transfus. Clin. Biol. 2001, 8, 291-296.
Daniels, J. S.; Pourmand, N. Label-free impedance biosensors: opportunities and challenges. Electroanalysis 2007, 19, 1239-1257.
De Giglio, E.; Sabbatini, L.; Zambonin, P. G. Development and analytical characterization of cysteine-grafted polypyrrole films electrosynthesized on Pt- and Ti-substrates as precursors of bioactive interfaces. J. Biomater. Sci. Polym. Ed. 1999, 10, 845-858.
Diaz-Gonzales M, Gonzalez-Garcia M B, Costa-Garcia A (2005) Recent advances in electrochemical enzyme immunoassays. Electroanalysis 17: 1901-1918.
Dill et al., "Antigen Detection Using Microelectrode Array Microchips" Analytica Chimica Acta, 2001, pp. 69-78, vol. 444.
Dill et al., "Immunoassays and Sequence-Specific DNA Detection on a Microchip . . . " J. Biochem. Biophys. Methods, 2004, 59 pp. 181-187, Elsevier B.V.
Dill K, Montgomery D D, Ghindilis A L, Schwarzkopf K R, Ragsdale S R, et al. (2004) Immunoassays based on electrochemical detection using microelectrode arrays. Biosensors & Bioelectronics 20: 736-742.
Drummond et al., "Electrochemical DNA Sensors" Nature Biotechnology Oct. 2003, 1192-1199, vol. 21, No. 10 Nature Publishing Group.
Egeland et al., "An Electrochemical Redox Couple Activitated by Microelectrodes for Confined Chemical Patterning of Surfaces" Analytical Chemistry (2002) vol. 74, pp. 1590-1596.
Fledler et al., "Diffusional Electrotitration: Generation of pH Gradients . . . " Analytical Chemistry, Mar. 1. 1995, pp. 820-828, vol. 67, No. 5.
Fodor et al., "Light-Directed, Spatially Addressable Parallel Chemical Synthesis" Science, Feb. 15, 1991, 767-773, vol. 251.
Galandoava, J.; Labuda, J. Polymer interfaces used in electrochemical DNA-based biosensors. Chem. Pap. 2009, 63, 1-14.
Gambhir, A.; Gerard, M.; Jain, S. K.; Malhotra, B. D. Characterization of DNA immobilized on electrochemically prepared conducting polypyrrole-polyvinyl sulfonate films. Appl. Biochem. Biotechnol. 2001, 96, 303-309.
Gao et al., "In Situ Synthesis of Oligonucleotide Microarrays" Biopolymers Mar. 2004, pp. 579-596, vol. 73.
Ghindilis et al., "Immunosensors: Electrochemical Sensing and Other . . . " Biosensors & Bioelectronics 1998, pp. 113-131, vol. 13, No. 1, Elsevier Sciences S.A.
Ghindilis, A. L.; Smith, M. W.; Schwarzkopf, K. R.; Roth, K. M.; Peyvan, K.; Munro, S. B.; Lodes, M. J.; Stover, A. G.; Bernards, K.; Dill, K.; McShea, A. CombiMatrix oligonucleotide arrays: genotyping and gene expression assays employing electrochemical detection. Biosens. Bioelectron. 2007, 22, 1853-1860.
Greene et al., "Protective Groups in Organic Synthesis" Third Edition, Wiley-Interscience, 1999.
Guo, et al., "Direct Fluorescence Analysis of Genetic Polymorphisms by Hybridization with Oligonucleotide . . . " Nucl. Acids Res., 1994, pp. 5456-5465, vol. 22, No. 24.
Hacia "Resequencing and mutational analysis using oligonucleotide microarrays" Nature Genetics 21 Supp.: 42, (1999).
Hacia et al., "Applications of DNA Chips for Genomic Analysis" Mol. Psychiatry, Nov. 1998, pp. 483-492, vol. 3, No. 6.
Hammerich et al., "Organic Electrochemistry, an Introduction & Guide" ed. by Lund and Baizer, 3rd Edition, 1991 pp. 615-657 Marcel Dekker, Inc., NY.
Johnston, "Gene Chips: Array of Hope for Understanding Gene Regulation" Curr. Biology, Feb. 26, 1998, R171-R174, vol. 8.
Krotz et al., "Large-Scale Synthesis of Antisense Oligonucleotides Without Chlorinated Solvents" Organic Process Res & Dev, 2000, pp. 190-193, vol. 4.
Kurian et al., "DNA Chip Technology" J. Pathology, 1999, pp. 267-271, vol. 187.
Labib M, Hedstrom M, Amin M, Mattiasson B (2009) A capacitive biosensor for detection of staphylococcal enterotoxin B. Anal Bioanal Chem 393: 1539-1544.
Lane et al., "Electrochemistry of Chemisorbed Molecules . . . " J. Physical Chemistry, 1973, pp. 1411-1421, vol. 77, No. 11 ($1^{st}$ Page Only).
Leproust et al., "Characterization of Oligodeoxyribonucleotide Synthesis on Glass Plates" Nucl. Acids Res., 2001, pp. 2171-2180, vol. 29, No. 10 (Abstract Only).
Livache, T.; Maillart, E.; Lassalle, N.; Mailley, P.; Corso, B.; Guedon, P.; Roget, A.; Levy, Y. Polypyrrole based DNA hybridization assays: study of label free detection processes versus fluorescence on microchips. J. Pharm. Biomed. Anal 2003, 32, 687-696.
Livache, T.; Fouque, B.; Roget, A.; Marchand, J.; Bidan, G.; Teoule, R.; Mathis, G. Polypyrrole DNA chip on a silicon device: example of hepatitis C virus genotyping. Anal. Biochem. 1998, 255, 188-194.
Livache, T.; Roget, A.; Dejean, E.; Barthet, C.; Bidan, G.; Teoule, R. Preparation of a DNA matrix via an electrochemically directed copolymerization of pyrrole and oligonucleotides bearing a pyrrole group. Nucleic. Acid. Res. 1994, 22, 2915-2921.
Lipkowski, et al., "Molecular Adsorption at Metal Electrodes" Electrochimica Acta, 1994, pp. 1045-1056, vol. 39, No. 8/9.
Maskos and Southern, "Oligodeoxyribonucleotide Synthesis on Glass Plates", Nucl. Acids Res., 1992, pp. 1679-1684, vol. 20.
Minehan, D. S.; Marx, K. A.; Tripathy, S. K. Kinetics of DNA binding to electrically conducting polypyrrole films. Macromolecules 1994, 27, 777-783.
Minehan, D. S.; Marx, K. A.; Tripathy, S. K. DNA binding to electropolymerized polypyrrole: The dependence on film characteristics. J. Macromol. Sci. Part A: Pure Appl. Chem. 2001, 38, 1245-1258.
Moller et al.. "Anodic oxidation of cyclohexene: Dependence of the product distribution on the reaction variables" Electrochimica Acta, vol. 42, No. 13, Jan. 1, 1997, pp. 1971-1978.
Ono et al., "Nucleosides and Nucleotides. 121. Synthesis of Oligonucleotides . . . " Bioconjugate Chem. 1993, pp. 499-508, vol. 4.
Palmisano F, Zambonin P G, Centoze D (2000) Amperometric biosensors based on electrosynthesised polymeric films. Fresenius Journal of Analytical Chemistry 366: 586-601.
Park, J. Y.; Park, S. M. DNA Hybridization sensors based on electrochemical impedance spectroscopy as a detection tool. Sensors 2009, 9, 9513-9532.
Patolsky et al. "Highly Sensitive Amplified Electronic Detection of DNA . . . " Chem. Eur. J., 2003, pp. 1137-1145, vol. 9, No. 5 Wiley-VCH Weinheim.
Patolsky et al., "Enzyme-Linked Amplified Electrochemical Sensing . . . " Langmuir 1999, vol. 15, No. 1,1 pp. 3703-3706, Am. Chemical Society.
Paul et al., "Acid Binding and Detritylation During Oligonucleotide Synthesis" Nucleic Acids Research, 1996, 3048-3052, vol. 24, No. 15.
Pellois et al., "Peptide Synthesis Based on t-Boc Chemistry & Solution Photogenerated Acids" J. Comb. Chem. 2000, pp. 355-360, vol. 2, No. 4.
Peng, H.; Zhang, L.; Soeller, C.; Travas-Sejdic, J. Conducting polymers for electrochemical DNA sensing. Biomaterials 2009, 30, 2132-2148.
Pillai, "Photoremovable Protecting Groups in Organic Chemistry" Synthesis 1980, pp. 1-26, vol. 39.
Rahman M A, Kumar P, Park D-S, Shim Y-B (2008) Electrochemical sensors based on organic conjugated polymers. Sensors 8: 118-141.
Ramanaviciene A, Ramanavicius A (2002) Application of polypyrrole for the creation of immunosensors. Critical Reviews in Analytical Chemistry 32: 245-252.
Ramanavicius A, Ramanaviciene A, Malinauskas A (2006) Electrochemical sensors based on conducting polymer-pyrrole. Electrochimica Acta 51: 6027-6037.
Ramanavicius, A.; Kurilcik, N.; Jursenas, S.; Finkelsteinas, A.; Ramanaviciene, A. Conducting polymer based fluorescence quenching as a new approach to increase the selectivity of immunosensors. Biosen. Bioelectron. 2007, 23, 499-505.

(56) References Cited

OTHER PUBLICATIONS

Ronlan, A. and Parker, V. D., "Anodic oxidation of phenolic compounds. Part II. Products and mechanisms of the anodic oxidation of hindered phenols" J. Chem. Soc. (C), 1971, pp. 3214-3218.
Roth, K. M.; Peyvan, K.; Schwarzkopf, K. R.; Ghindilis, A. Electrochemical detection of short dna oligomer hybridization using the combimatrix electrasense microarray reader. Electroanalysis 2006, 18, 1982-1988.
Rossier et al., "Enzyme Linked Immunsorbent Assay on a Microchip . . . " Lab on a Chip 2001, vol. 1, pp. 153-157, The Royal Society of Chemistry.
Sadik O A, Ngundi M, Wanekaya A (2003) Chemical biological sensors based on advances in conducting electroactive polymers. Microchimica Acta 143: 187-194.
Sadki S, Schottland P, Brodie N, Sabouraud G (2000) The mechanisms of pyrrole electropolymerization. Chemical Society Review 29: 283-293.
Septak, M. "Kinetic Studies on Depurination and Detritylation of CPG-bound Intermediates . . . " Nucleic Acids Research, 1996, pp. 3053-3058, vol. 24, No. 15.
Shchepinov et al., "Steric Factors Influencing Hybridisation of Nucleic Acids to Oligonucleotide Arrays" Nucl., Acids Res., 1997, pp. 115-1161, vol. 25, No. 6.
Shchepinov, M.S., "Oligonucleotide Dendrimers: From Poly-Labeled DNAc617 Probes to Stable Nano-Structures" Glen Report, Dec. 1999, vol. 12, No. 1.
Song, X.; Wang, H. L.; Shi, J.; Park, J. W.; Swanson, B. I. Conjugated polymers as efficient fluorescence quenchers and their applications for bioassays. Chem. Mater. 2002, 14, 2342-2347.
Soriaga et al., "Determination of Orientation of Adsorbed Molecules . . . ", J. Am. Chem. Soc., 1982, pp. 3937-3945, vol. 104 ($1^{st}$ Page Only).
Stickney et al., "A Survey of Factors Influencing the Stablity of . . . " J. Electroanaly. Chem., 1981, pp. 73-88, vol. 125 (Abstract Only).
Stuart, M.; Maurer, K.; Moeller, K. D. Moving known libraries to an addressable array: A site-selective hetero-Michael reaction. Bioconjug. Chem. 2008, 19, 1514-1517.
Tesfu, E.; Roth, K.; Maurer, K.; Moeller, K. D. Building addressable libraries: Site selective coumarin synthesis and the "real-time" signaling of antibody-coumarin binding. Org. Lett. 2006, 8, 709-712.
Trojanowicz M (2003) Application of conducting polymers in chemical analysis. Microchimica Acta 143: 75-91.
Vestergaard Md, Kerman K, Tamiya E (2007) An overview of label-free electrochemical protein sensors. Sensors 7: 3442-3458.
Vidal J-C, Garcia-Ruiz E, Castillo J-R (2003) Recent Advances in electropolymerized conducting polymers in amperometric biosensors. Microchimica Acta 143.
Wang, G. et al., "Synthesis of Oligonucleotides Containing . . . " Tetrahedron Letters, 1993, 6721-6724, vol. 34, No. 42, Great Britain.
Wang et al., "Dual Enzyme Electrochemical Coding for Detecting DNA Hybridization" Analyst 2002, 1279-1282, The Royal Society of Chemistry.
Wang, Joseph "Survey and Summary from DNA Biosensors . . . " Nucleic Acids Research 2000, pp. 3011-3016, vol. 28, No. 16 Oxford University Press.
Wilgenbus and Lichter, "DNA Chip Technology Ante Portas" J. Mol. Med., Nov. 1999, pp. 761-768, vol. 77.
Wu and Chen, J. Mater. Chem., 1997, 7(8), pp. 1409-1413.
Xie et al., Amperometric Detection of Nucleic Acid at Femtomolar Levels with a Nucleic Acid/Electrochemical Activator Bilayer on Gold Electrodes, 2004, vol. 76, pp. 1611-1617.
Zhang S, Wright G, Yang Y (2000) Materials and techniques for electrochemical biosensor design and construction. Biosensors & Bioelectronics 15: 273-282.
Zhou, Y.; Yu, B.; Guiseppi-Elie, A.; Sergeyev, V.; Levon, K. Potentiometric monitoring DNA hybridization. Biosens. Bioelectron. 2009, 24, 3275-3280.
Article 94(3) European Communication, Application No. 05849631.6 PCT/US2005/041906, dated Jan. 30, 2018, 4 pages.
Response to Article 94(3) European Communication, Application No. 05849631.6 PCT/US2005/041906, dated May 22, 2018, 3 pages.
Amended Claims filed in response to Article 94(3) European Communication, Application No. 05849631.6 , PCT/US2005/041906, dated May 22, 2018, 4 pages.
Amendment filed in response to Rule 115(1) EPC Communication, Application No. 06739757.0 PCT/US2006/011150, dated Dec. 18, 2018, 6 pages.
Auxiliary Request II Claims filed in response to Rule 115(1) EPC Communication, Application No. 06739757.0 PCT/US2006/011150, dated Dec. 18, 2018, 1 page.
Communication from the examining division, Application No. 06739757.0 PCT/US2006/011150, dated Jan. 11, 2019, 2 pages.

* cited by examiner

Ricin LLD: Fluorescent and ECD detecion on same chip

4012568 cy5 FL detect
- 1.3V
- 1.4V
- 1.5V
- 1.7V

Fluorescence vs Rcin pg/mL (0, 0.1, 1, 10)

ECD detect Ricin: 4012568
- 1.3V
- 1.4V
- 1.5V
- 1.7V

ECD units vs Rcin pg/mL (0, 0.1, 1, 10)

ECD / FL images at 10, 1, 0.1, 0 pg/mL

Fig. 16

Antigen immobilization: Ricin Titration

PPY depo V  1.0  1.3  1.4  1.5  1.7

Pyrole CN
Ricin 10 ug/ml
Ricin 10 ng/mL
Ricin 10 pg/mL

Antibody Conc.
20ug/ml
20ng/ml
20pg/ml
0

Fig. 17

SERIALLY DEPOSITED BIOMOLECULES

PRIORITY CLAIM

The present application is a continuation of (1) U.S. patent application Ser. No. 12/930,977, entitled "Multiplex Microarray of Serially Deposited Biomolecules on a Microarray" filed Jan. 20, 2011, which claims priority to (2) U.S. Provisional Patent Application No. 61/336,386, filed Jan. 20, 2010, of which application is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CUST-01001US2_ST25.TXT, created Mar. 23, 2018, 1140 bytes, machine format IBM-PC, MS-Windows operating system, is hereby incorporated by reference.

TECHNICAL FIELD

The disclosure herein relates to a microarray of serially deposited biomolecules on a CMOS microarray and a method of making the same. The CMOS microarray has an array of microelectrodes on its surface and polypyrrole electropolymerized on the surface of the microelectrodes with the biomolecules attached to the polypyrrole. The biomolecules include DNA, RNA, proteins, antibodies, antigens, and other biomolecules. The microarray can be used in biomedical and biotechnology research as well as in diagnostic applications.

BACKGROUND

The COMBIMATRIX CUSTOMARRAY® microarray and ElectraSense microarray are complementary metal oxide semiconductor (CMOS) chips with 12,544 electrodes that can be addressed individually or in user-defined groups. These arrays are available commercially as custom DNA chips with different nucleic acid probe sequences produced at each electrode using sequential electrochemical reactions to add phosphoramidites (Maurer K, Cooper J, Caraballo M, Crye J, Suciu D, et al. (2006) Electrochemically generated acid and its containment to 100 micron reaction areas for the production of DNA microarrays. PLoS ONE 1). Hybridization to probes can be detected using cyanine (Cy) dyes and fluorescent scanners or, alternatively, using horseradish peroxidase (HRP) and enzyme-enhanced electrochemical detection (ECD) on CombiMatrix's microarray readers.

In a paper, a method was first described for fixing capture antibodies (Abs) on the 1000-electrode CustomArray microarray, a predecessor of the current ElectraSense microarray (Dill K, Montgomery D D, Wang W, Tsai J C (2001) Antigen detection using microelectrode array microchips. Analytica Chimica Acta 444: 69-78.) Disclosed in this paper is a synthesis of different DNA probes on individual electrodes and use of Abs tagged with complementary oligonucleotides to self-assemble specifically on individual electrodes of the multiplex array. The array had capture Abs against ricin, Bacillus globigii spores, M13 phage, .alpha.1 acid glycoprotein, and fluorescein. Initially, antigen (Ag) binding was measured optically, using fluorophore-labeled target or reporter Ab. However, in later studies, amperometry was used along with HRP, peroxide, and ortho-phenylenediamine (Dill K, Montgomery D D, Ghindilis A L, Schwarzkopf K R (2004) Immunoassays and sequence-specific DNA detection on a microchip using enzyme amplified electrochemical detection. Journal of biochemical and biophysical methods 59: 181-187; Dill K, Montgomery D D, Ghindilis A L, Schwarzkopf K R, Ragsdale S R, et al. (2004) Immunoassays based on electrochemical detection using microelectrode arrays. Biosensors & Bioelectronics 20: 736-742.) These studies reported that the multiplex microarray and assay demonstrated high specificity and sensitivity in the low pg/ml range. However, a problem with current immunoassays is that the conjugated Abs are fragile, expensive, and difficult to produce reliably. Thus, there is a need in the art to provide an immunoassay that uses more robust, less expensive, and easier to produce Abs. Studies have used a constant voltage with a two compartment electrochemical cell where a reference electrode can maintain the applied voltage. In one study, the authors reported that using a potential pulse technique with a range of 0.6 to 1.2 V versus Ag/AgCl for initial structuring of the Ppy was most suitable for entrapping biologically active materials (Ramanavicius A, Ramanaviciene A, Malinauskas A (2006) Electrochemical sensors based on conducting polyer-pyrrole. Electrochimica Acta 51: 6027-6037).

A study reviewed the physical, electrical and chemical parameters that influence the electropolymerization of pyrrole and identified monomer substitution, electrolyte (dopant), solvent, pH, electrochemical method, and temperature as influencing the formation and characteristics of a Ppy film (Sadki S, Schottland P, Brodie N, Sabouraud G (2000) The mechanisms of pyrrole electropolymerization. Chemical Society Review 29: 283-293).

Ppy belongs to a family of conducting polymers that includes polythiophene and polyaniline, each of which have been used to fix proteins and other biomolecules to electrodes for detection using different electrochemical methods. (Cosnier S (1999) Biomolecule immobilization on electrode surfaces by entrapment or attachment to electrochemically polymerized films. A review. Biosensors & Bioelectronics 14: 443-456; Zhang S, Wright G, Yang Y (2000) Materials and techniques for electrochemical biosensor design and construction. Biosensors & Bioelectronics 15: 273-282; Palmisano F, Zambonin P G, Centoze D (2000) Amperometric biosensors based on electrosynthesised polymeric films. Fresenius Journal of Analytical Chemistry 366: 586-601; Ramanaviciene A, Ramanavicius A (2002) Application of polypyrrole for the creation of immuno sensors. Critical Reviews in Analytical Chemistry 32: 245-252; Vidal J-C, Garcia-Ruiz E, Castillo J-R (2003) Recent Advances in electropolymerized conducting polymers in amperometric biosensors. Microchimica Acta 143; Trojanowicz M (2003) Application of conducting polymers in chemical analysis. Microchimica Acta 143: 75-91; Sadik O A, Ngundi M, Wanekaya A (2003) Chemical biological sensors based on advances in conducting electroactive polymers. Microchimica Acta 143: 187-194; Vestergaard Md, Kerman K, Tamiya E (2007) An overview of label-free electrochemical protein sensors. Sensors 7: 3442-3458; Rahman M A, Kumar P, Park D-S, Shim Y-B (2008) Electrochemical sensors based on organic conjugated polymers. Sensors 8: 118-141; Bakker E (2004) Electrochemical sensors. Anal Chem 76: 3285-3298; Diaz-Gonzales M, Gonzalez-Garcia M B, Costa-Garcia A (2005) Recent advances in electrochemical enzyme immunoassays. Electroanalysis 17: 1901-1918; Ramanavicius A, Ramanaviciene A, Malinauskas A (2006) Electrochemical sensors based on conducting polyer-pyrrole. Electrochimica Acta 51: 6027-6037.) In one study, Ppy was identified for its biocompatibility, its ability to transduce energy into electrical signals, its protective properties against electrode fouling, and its potential for in situ modification (Ramanaviciene A, Ramanavicius A (2002) Application of polypyrrole for the creation of immunosensors. Critical Reviews in Analytical Chemistry 32: 245-252.)

The CombiMatrix microarray with 12,544 microelectrodes supports in situ electrochemical synthesis of user-defined DNA probes. CombiMatrix microarrays were initially developed as highly multiplexed platforms for electrochemistry. The original complementary metal oxide (CMOS) microarray had 1,000 platinum (Pt) electrodes (1K microarray), and it was used to develop the in situ electrochemical synthesis of different DNA probes on individual electrodes (Maurer, K.; Cooper, J.; Caraballo, M.; Crye, J.; Suciu, D.; Ghindilis, A.; Leonetti, J. A.; Wang, W.; Rossi, F. M.; Stover, A. G.; Larson, C.; Gao, H.; Dill, K.; McShea, A. Electrochemically generated acid and its containment to 100 micron reaction areas for the production of DNA microarrays. PLoS One 2006, 1, 34). Hybridization to these probes was detected using enzyme-enhanced electrochemical detection (ECD) (Dill, K.; Montgomery, D. D.; Ghindilis, A. L.; Schwarzkopf, K. R. Immunoassays and sequence-specific DNA detection on a microchip using enzyme amplified electrochemical detection. J Biochem. Biophys. Methods 2004, 59, 181-187). The second generation microarray with 12,544 electrodes was mounted in a ceramic slide that was designed so that the chip could be read on a commercial fluorescent microarray reader. The 12K CUSTOMARRAY® microarray is commercially available as a custom gene chip that has been used for a variety of genomic assays (e.g., genotyping, gene expression, SNP analysis, etc.). CombiMatrix also developed the ELECTRASENSE® microarray and microarray reader based on ECD. In comparative studies, ECD provides comparable results to fluorescence detection (Roth, K. M.; Peyvan, K.; Schwarzkopf, K. R.; Ghindilis, A. Electrochemical detection of short dna oligomer hybridization using the combimatrix electrasense microarray reader. Electroanalysis 2006, 18, 1982-1988; Ghindilis, A. L.; Smith, M. W.; Schwarzkopf, K. R.; Roth, K. M.; Peyvan, K.; Munro, S. B.; Lodes, M. J.; Stover, A. G.; Bernards, K.; Dill, K.; McShea, A. CombiMatrix oligonucleotide arrays: genotyping and gene expression assays employing electrochemical detection. Biosens. Bioelectron. 2007, 22, 1853-1860). The latest version of the ElectraSense microarray reader is a palm-sized instrument that interfaces with a personal computer through a USB connection, which provides a data link and power to the reader.

The microarray offers unique capabilities for applications where the electrochemical synthesis or deposition of different molecules on electrodes and different methods of detection are required. The 1K microarray was used to synthesize coumarin or to demonstrate a site-selective hetero-Michael reaction on individual electrodes (Tesfu, E.; Roth, K.; Maurer, K.; Moeller, K. D. Building addressable libraries: Site selective coumarin synthesis and the "real-time" signaling of antibody-coumarin binding. Org. Lett. 2006, 8, 709-712; Stuart, M.; Maurer, K.; Moeller, K. D. Moving known libraries to an addressable array: A site-selective hetero-Michael reaction. Bioconjug. Chem. 2008, 19, 1514-1517). Successful execution of these chemistries was determined using fluorescence detection and cyclic voltammetry (CV). The array has been used with fluorescence detection and time-of-flight secondary ion mass spectrometry to demonstrated molecular synthesis using Wacker oxidations (Chen, C.; Nagy, G.; Walker, A. V.; Maurer, K.; McShea, A.; Moeller, K. D. Building addressable libraries: The use of a mass spectrometry cleavable linker for monitoring reactions on a microelectrode array. J. Am. Chem. Soc. 2006, 128, 16020-16021).

Immobilizing DNA to electrode surfaces using Ppy was originally reported by Minehan et al. (Minehan, D. S.; Marx, K. A.; Tripathy, S. K. Kinetics of DNA binding to electrically conducting polypyrrole films. Macromolecules 1994, 27, 777-783). Since that finding, numerous studies have been done using this and other electroactive polymers as described in recent reviews (Bakker, E. Electrochemical sensors. Anal. Chem. 2004, 76, 3285-3298; Daniels, J. S.; Pourmand, N. Label-free impedance bio sensors: opportunities and challenges. Electroanalysis 2007, 19, 1239-1257; Rahman, M.; Kumar, P.; Park, D. S.; Shim, Y. B. Electrochemical sensors based on organic conjugated polymers. Sensors 2008, 8, 118-141; Peng, H.; Zhang, L.; Soeller, C.; Travas-Sejdic, J. Conducting polymers for electrochemical DNA sensing. Biomaterials 2009, 30, 2132-2148; Galandoava, J.; Labuda, J. Polymer interfaces used in electrochemical DNA-based biosensors. Chem. Pap. 2009, 63, 1-14; Batchelor-McAuley, C.; Wildgoose, G. G.; Compton, R. G. The physicochemical aspects of DNA sensing using electrochemical methods. Biosens. Bioelectron. 2009, 24, 3183-3190; Park, J. Y.; Park, S. M. DNA Hybridization sensors based on electrochemical impedance spectroscopy as a detection tool. Sensors 2009, 9, 9513-9532.)

Most of the studies reported on using label less detection (e.g., CV and electrochemical impedance spectroscopy) for measuring DNA hybridization. More relevant to our findings are those reported by investigators at CIS Bio international and CEA (Livache, T.; Roget, A.; Dejean, E.; Barthet, C.; Bidan, G.; Teoule, R. Preparation of a DNA matrix via an electrochemically directed copolymerization of pyrrole and oligonucleotides bearing a pyrrole group. Nucleic. Acid. Res. 1994, 22, 2915-2921; Livache, T.; Fouque, B.; Roget, A.; Marchand, J.; Bidan, G.; Teoule, R.; Mathis, G. Polypyrrole DNA chip on a silicon device: example of hepatitis C virus genotyping. Anal. Biochem. 1998, 255, 188-194; Caillat, P.; David, D.; Belleville, M.; Clerc, F.; Massit, C.; Revol-Cavalier, F.; Peltie, P.; Livache, T.; Bidan, G.; Roget, A.; Crapez, E. Biochips on CMOS: An active matrix address array for DNA analysis. Sens. Actuat. B: Chem. 1999, 61, 154-162; Cuzin, M. DNA chips: A new tool for genetic analysis and diagnostics. Transfus. Clin. Biol. 2001, 8, 291-296; Livache, T.; Maillart, E.; Lassalle, N.; Mailley, P.; Corso, B.; Guedon, P.; Roget, A.; Levy, Y. Polypyrrole based DNA hybridization assays: study of label free detection processes versus fluorescence on microchips. J. Pharm. Biomed. Anal 2003, 32, 687-696.) This group developed a CMOS microarray with 128 addressable electrodes, and they co-polymerized pyrrole with pyrrole-conjugated DNA probes to create a multiplexed gene chip for the fluorescence detection of hybridization.

A number of investigators have relied on entrapment to immobilize unmodified DNA to Ppy; however, more have modified the DNA, the Ppy, or both to create a covalent attachment between one end of the DNA (usually the 5'-end) and the Ppy. This provides a secure and oriented fixation of the DNA to the Ppy that is often illustrated as a lawn of vertical strands standing perpendicular to the Ppy (Peng, H.; Zhang, L.; Soeller, C.; Travas-Sejdic, J. Conducting polymers for electrochemical DNA sensing. Biomaterials 2009, 30, 2132-2148.)

Minehan et al. and Gambhir et al. reported that the binding of DNA to Ppy is consistent with electrostatic adsorption between the fixed negatively charged phosphates forming the backbone of the DNA and the mobile positively charged defect structures of the Ppy, which favor hydrogen bonding between the phosphates and Ppy ring nitrogen atoms (Minehan, D. S.; Marx, K. A.; Tripathy, S. K. DNA binding to electropolymerized polypyrrole: The dependence on film characteristics. J. Macromol. Sci. Part A: Pure Appl. Chem. 2001, 38, 1245-1258; Gambhir, A.; Gerard, M.; Jain, S. K.; Malhotra, B. D. Characterization of DNA immobilized on electrochemically prepared conducting polypyrrole-polyvinyl sulfonate films. Appl. Biochem. Biotechnol. 2001, 96, 303-309). However, De Giglio et al. demonstrated that cysteine binds to Ppy electropolymerized on platinum or titanium electrodes (De Giglio, E.; Sabbatini, L.; Zambonin, P. G. Development and analytical characterization of cysteine-grafted polypyrrole films electrosynthesized on Pt- and Ti-substrates as precursors of bioactive interfaces. J. Biomater. Sci. Polym. Ed. 1999, 10, 845-858). They presented evidence from X-ray photoelectron spectroscopy that cysteine forms a covalent bond through its sulfur atom by nucleophilic attack on the positive sites of the pyrrole ring. More recently, Zhou et al. reported on immobilizing 5'cys-terminated DNA probes to electropolymerized polyaniline via a nucleophilic substitution reaction and measuring hybridization using CV (Zhou, Y.; Yu, B.; Guiseppi-Elie, A.; Sergeyev, V.; Levon, K. Potentiometric monitoring DNA hybridization. Biosens. Bioelectron. 2009, 24, 3275-3280).

Ramanvicius et al. used Ppy fluorescence quenching to develop an immunoassay against bovine leukemia virus protein gp51 (Ramanavicius, A.; Kurilcik, N.; Jursenas, S.; Finkelsteinas, A.; Ramanaviciene, A. Conducting polymer based fluorescence quenching as a new approach to increase the selectivity of immunosensors. Biosen. Bioelectron. 2007, 23, 499-505). They attributed the quenching to the proximity of the Cy5 to the delocalized .pi.-.pi. electrons in the Ppy backbone, as described by Song et al. (Song, X.; Wang, H. L.; Shi, J.; Park, J. W.; Swanson, B. I. Conjugated polymers as efficient fluorescence quenchers and their applications for bioassays. Chem. Mater. 2002, 14, 2342-2347). Livache et al. did not describe fluorescence quenching by Ppy in their development of a DNA chip that used phycoerythrin as the fluorescent marker; however, they did note that fluorescence increased with increasing Ppy thickness and with a T-linker of increasing length between the pyrrole and the oligonucleotide 5' end (Livache, T.; Fouque, B.; Roget, A.; Marchand, J.; Bidan, G.; Teoule, R.; Mathis, G. Polypyrrole DNA chip on a silicon device: example of hepatitis C virus genotyping. Anal. Biochem. 1998, 255, 188-194). The Ppy thickness used by these investigators was 20 nm, which was produced by dipping the electrode in 20 mM pyrrole with 1 µM pyrrole-conjugate oligonucleotide and electro-copolymerizing them using CV until a charge of 250 nC was reached.

Neoh et al. [29] and Ando et al. [30] reported that elevated temperatures (100-200° C.) reduced the conductivity of Ppy through a number of possible mechanisms.

SUMMARY

1. In an embodiment, a method of making a multiplex microarray of serially attached different biomolecules on a microarray is disclosed. The method comprises: (a) blocking a microarray with a blocking protein, wherein the microarray is a device having an array of addressable microelectrodes on a surface of the device; (b) electropolymerizing monomer on one or more microelectrodes of the microarray to form a polymer coating on the one or more microelectrodes, wherein an electropolymerizing solution containing the monomer does not contain any of the biomolecules; (c) exposing the microarray to a biomolecular solution containing a biomolecule for attachment to the polymer coating on the one or more electrodes, wherein the biomolecule is not an oligonucleotide and is not chemically functionalized; (d) blocking the microarray with a blocking protein; and (e) repeating steps (b) through (d) for each different biomolecule to be attached to the microarray, thereby making the microarray of different biomolecules. In an embodiment, steps (a) and (d) further comprise: washing the microarray to remove the blocking solution. In an embodiment, the step of washing to remove the blocking solution comprises: washing about three times with PBS/Tween, about three times with PBS, and about three times with the electrolyte used for the polymerization of pyrrole. In an embodiment, step (b) further comprises: washing the microarray to remove the electropolymerizing solution. In an embodiment, the step of washing to remove the electropolymerizing solution comprises: washing about three times with PBS. In an embodiment, step (c) further comprises: washing the microarray to remove the biomolecular solution. In an embodiment, the step of washing to remove the biomolecular solution comprises: washing about three times with PBS. In an embodiment, the biomolecules are selected from the group consisting of antibodies, antigens, proteins, Ricin, anti-SEB MAb, enzymes, and HRP, and combinations thereof. In an embodiment, the biomolecules are selected from the group consisting of carbohydrates, sugars, dextrane, PEG, and poly-L-lysine and combinations thereof. In an embodiment, the blocking protein is selected from the group consisting of Casein and Bovine Calf Serum and combinations thereof, and the blocking time is about 2 to about 5 minutes. In an embodiment, the step of electropolymerizing further comprises: activating the at least one of the microelectrodes for about five seconds at about 1.5 V using sodium phosphate as the electrolyte for the electropolymerizing solution. In an embodiment, the step of exposing further comprises: exposing for about 5 to about 30 minutes and the concentration of the biomolecule is about 1 µg/ml. In an embodiment, the device is a CMOS device. In an embodiment, the monomer is selected from the group consisting of pyrrole and functionalized pyrrole and combinations thereof. In an embodiment, the monomer is selected from the group consisting of thiophenol, aniline, phenylene sulfide, monomers electropolymerizing to a conducting polymer, phenylenediamine, diaminohaphthalene, phenol, monomers electropolymerizing to a nonconducting polymer and phenolic derivatives, and combinations thereof. In an embodiment, the step of exposing the microarray to a biomolecular solution is incubation/submersion in a biomolecular solution. In an embodiment, the step of exposing the microarray to a biomolecular solution is spotting on the biomolecular solution.

In an embodiment, a microarray for a multiplex assay is disclosed and comprises: (a) a microarray having on a surface an array of addressable microelectrodes having an exposed surface; (b) an electropolymerized polymer attached to the exposed surface of the microelectrodes; and (c) a plurality of different non-functionalized biomolecules attached to the polymer at different microelectrodes of the microarray, wherein the biomolecules are selected from the group consisting of antibodies, antigens, proteins, Ricin, anti-SEB MAb, enzymes, and HRP and combinations thereof. In an embodiment, the microarray is a CMOS device. In an embodiment, the polymer is made by electropolymerizing a monomer that is selected from the group consisting of pyrrole and functionalized pyrrole and combinations thereof. In an embodiment, the polymer is made by electropolymerizing a monomer that is selected from the group consisting of thiophenol, aniline, phenylene sulfide, monomers electropolymerizing to a conducting polymer, phenylenediamine, diaminohaphthalene, phenol, monomers electropolymerizing to a nonconducting polymer and phenolic derivatives, and combinations thereof.

In an embodiment, a method of making a multiplex microarray of serially attached different oligonucleotides on a microarray is disclosed and comprises: (a) blocking a microarray with a blocking protein, wherein the microarray is a device having an array of addressable microelectrodes on a surface of the device; (b) electropolymerizing a monomer on one or more microelectrodes of the microarray to form a polymer coating on the one or more microelectrodes, wherein an electropolymerizing solution containing the monomer does not contain any of the biomolecules; (c) exposing the microarray to an oligonucleotide solution containing an oligonucleotide for attachment to the polymer coating on the one or more electrodes; (d) blocking the microarray with a blocking protein; and (e) repeating steps (b) through (d) for each different biomolecule to be attached to the microarray, thereby making the microarray of different biomolecules. In an embodiment, steps (a) and (d) further comprise: washing the microarray to remove the blocking solution. In an embodiment, the step of washing to remove the blocking solution comprises: washing about three times with PBS/Tween, about three times with PBS, and about three times with the electrolyte used for the polymerization of pyrrole. In an embodiment, step (b) further comprises: washing the microarray to remove the electropolymerizing solution. In an embodiment, the step of washing to remove the electropolymerizing solution comprises: washing about three times with PBS. In an embodiment, step (c) further comprises: washing the microarray to remove the biomolecular solution. In an embodiment, the step of washing to remove the biomolecular solution comprises: washing about three times with PBS. In an embodiment, the blocking protein is selected from the group consisting of Casein and Bovine Calf Serum and combinations thereof, and the blocking time is about 2 to about 5 minutes. In an embodiment, the step of electropolymerizing further comprises: activating the at least one of the microelectrodes for about five seconds at about 1.5 V using sodium phosphate as the electrolyte for the electropolymerizing solution. In an embodiment, the step of exposing further comprises: exposing for about 5 to about 30 minutes and the concentration of the biomolecule is about 1 µg/ml. In an embodiment, the device is a CMOS device. In an embodiment, the monomer is selected from the group consisting of pyrrole and functionalized pyrrole and combinations thereof. In an embodiment, the monomer is selected from the group consisting of thiophenol, aniline, phenylene sulfide, monomers electropolymerizing to a conducting polymer, phenylenediamine, diaminohaphthalene, phenol, monomers electropolymerizing to a nonconducting polymer and phenolic derivatives, and combinations thereof. In an embodiment, the step of exposing the microarray to a biomolecular solution is incubation/submersion in a biomolecular solution. In an embodiment, the step of exposing the microarray to a biomolecular solution is spotting on the biomolecular solution.

In an embodiment, a microarray for a multiplex oligonucleotide hybridization assay is disclosed and comprises: (a) a microarray having on a surface an array of addressable microelectrodes having an exposed surface; (b) an electropolymerized polymer attached to the exposed surface of the microelectrodes; and (c) a plurality of different preformed oligonucleotides serially-attached to the polymer at different microelectrodes of the microarray, wherein the different preformed oligonucleotides are not synthesized in situ on the microarray. In an embodiment, the microarray is a CMOS device. In an embodiment, the polymer is made by electropolymerizing a monomer that is selected from the group consisting of pyrrole and functionalized pyrrole and combinations thereof. In an embodiment, the polymer is made by electropolymerizing a monomer that is selected from the group consisting of thiophenol, aniline, phenylene sulfide, monomers electropolymerizing to a conducting polymer, phenylenediamine, diaminohaphthalene, phenol, monomers electropolymerizing to a nonconducting polymer and phenolic derivatives, and combinations thereof.

BRIEF DESCRIPTION OF THE DRAWINGS

FIG. 16. A figure that shows results of fluorescent and electrochemical detection of Ricin on a microarray of electrodes coated with Ppy.

FIG. 17. An image that shows the results of positive binding for Ricin to the polypyrrole deposited on the electrodes of the microarray.

DETAILED DESCRIPTION

Figure 1:
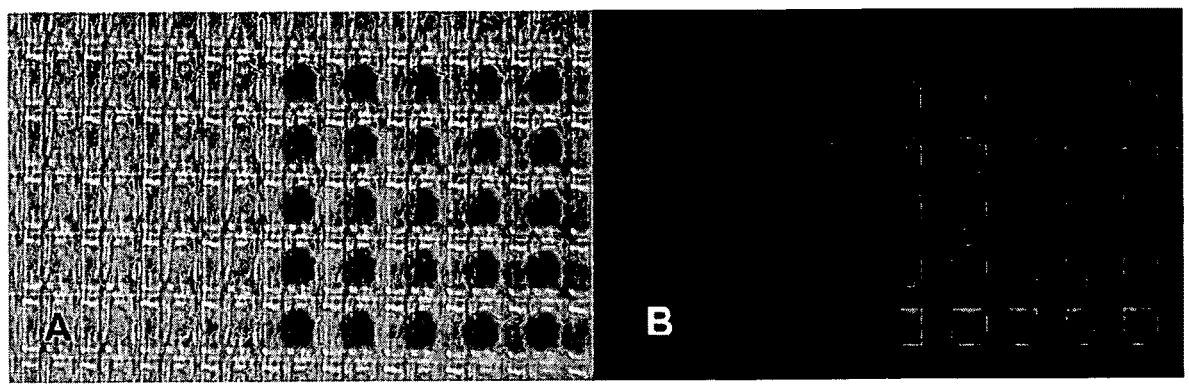
FIG. 1. Deposition of Ppy and Ab on individual electrodes. A) Photograph of the surface of a microarray showing the deposition of polypyrrole with adsorbed murine Ab on a 5×5 set of electrodes. B) Fluorescence scanned image, using Cy5-labeled goat anti mouse IgG, showing the presence of murine MAB on the electrodes.

Disclosed herein in an embodiment is an empirical method for developing and optimizing immunoassays on a microarray of individually addressable (serial or parallel or in groups) microelectrodes based upon selected deposition of polypyrrole (Ppy) and capture antibody (Ab). In an embodiment, the array is a COMBIMATRIX ELECTRASENSE® microarray, which is a complementary metal oxide semiconductor (CMOS.) This CMOS microarray has 12,544 electrodes and was used with instrumentation that can selectively apply a potential or current to individual electrodes and also measure current generated at the electrodes by an enzyme-enhanced electrochemical (ECD) reaction. By designating groups of electrodes on the array for different Ppy deposition conditions, the sensitivity and specificity of a sandwich immunoassay was determined for staphylococcal enterotoxin B (SEB) and was found to be influenced by the application of different voltages or currents and the application time. The sandwich immunoassay used a capture Ab adsorbed to the Ppy and a reporter Ab labeled for, in an embodiment, fluorescence detection or, in an embodiment, ECD. The results from these two embodiments of detection were different. Using Ppy deposition conditions for optimum results, the lower limit of detection for SEB using the ECD assay was between 0.003 and 0.01 pg/ml, which is an order of magnitude improvement over a conventional enzyme-linked immunosorbant assay. In the absence of understanding the variables and complexities that affect assay performance, this highly multiplexed electrode array provided a rapid, high throughput, and empirical approach for developing a sensitive immunoassay.

In an embodiment, polypyrrole (Ppy) is used to attached/adsorb Abs to individual electrodes on the array, where the electrodes have the Ppy attached to their surface and the Abs attached/adsorbed to the Ppy. In an embodiment, a CombiMatrix ElectraSense microarray is used with manual and automated instrumentation for the selective electrochemical deposition of Ppy and adsorption of capture Abs. By designating groups of electrodes on the array for different Ppy deposition conditions, the use of constant voltage or constant current and the length of time for Ppy deposition was determined to influence the sensitivity and specificity of an immunoassay for staphylococcal enterotoxin B (SEB) as measured using a secondary Ab labeled with Cy5 for fluorescence detection or HRP for ECD. Under optimum conditions, the ECD immunoassay was at least an order of magnitude more sensitive than an ELISA plate immunoassay.

Further disclosed herein in an embodiment is a highly multiplexed CMOS microarray for the automated deposition of Ppy and adsorption of capture Abs for detection of antigen binding using ECD or fluorescence detection. To support multiple assays and high throughput on the array, a microarray was physically divided into four chambers that accommodated different concentrations of Ag; and within each chamber, Ppy deposition could be controlled on >100 blocks of 4 electrodes with respect to time of deposition and voltage or current. In this configuration, a single microarray could support >400 different experimental conditions with respect to Ppy deposition and Ag concentrations. Moreover, Ag binding could be studied using an enzyme-enhanced ECD or fluorescence detection. The ability to perform such a large number of individual experiments in parallel demonstrates the power of this methodology. Attempting these studies using a single Pt electrode mounted in an electrochemical cell might provide good control over electrochemical processes but would lack throughput and versatility.

In an embodiment, a constant voltage is used to electropolymerize the Ppy. SEB detection was observed only when the Ppy was deposited between 0.7 and 1.9 V. While constant voltage was used successfully for electropolymerizing pyrrole, deposition voltages are affected by the number of electrodes addressed and were difficult to maintain using the MX300 in the absence of a reference electrode. However, in another embodiment, using this instrument with current sourcing provided consistent, automated deposition of Ppy and capture Ab because constant current could be maintained at each electrode regardless of the number of electrodes addressed. SEB detection using ECD is achieved by applying a low current (30-50 nA) for very brief periods of time (~1 s). Using fluorescence detection, the SEB assay performed well over even broader range of Ppy deposition currents.

From a practical standpoint of developing an optimized immunoassay using Ppy, monomer substitution, electrolyte (dopant), solvent, pH, electrochemical method, and temperature can be studied efficiently and effectively using the ElectraSense microarray and either the PotentioSense or MX300 instruments. Assay sensitivities can vary considerably with Ppy deposition time and voltage or current. Non-specific binding to the Ppy also appears to vary with deposition conditions. Those that produce optimal ECD sensitivities may differ from those providing optimal fluorescence detection.

Photomicrographs of Ppy deposition on electrodes illustrate additional factors that can influence the performance of ECD and fluorescent assays. With constant voltage deposition, appearance of colored Ppy spots roughly corresponded to the results of the ECD and fluorescent assays with detection occurring on Ppy deposited between 0.7 and 1.9 V. However, with constant current, the best ECD results occurred on Ppy deposited at low current for short periods of time and were colorless on the micrographs, whereas the best fluorescent results peaked at higher currents (220 nA) where colored Ppy began to appear. Although no efforts were made to identify the source of these differences and without being bound by theory, the two methods of detection likely are being influenced differently by the Ppy layer. For instance, thin films of electroactive Ppy should facilitate ECD by supporting electron transfer. At the same time, fluorescence detection may be reduced in thinner films because of fluorescence quenching by the Pt. Alternatively, more densely colored films of Ppy could also quench fluorescence, while a thicker, more oxidized Ppy layer that might provide more resistance to ECD With respect to the performance of the microarray as a platform for detecting SEB, the LOD for ECD assay was between 0.003 and 0.01 pg/ml under optimum conditions and no interferants. This was at least an order of magnitude better than that observed using a standard microtiter plate ELISA with the same Ab reagents. Staphylococcal enterotoxin B is a potent toxin and has been studied extensively because of its association with foodborne illnesses and use as a biological threat agent. One study listed the different immunoassays that have been developed to detect SEB and their LODs, which ranged from ~0.1 fg/ml to ~2.5 µg/ml (Labib M, Hedstrom M, Amin M, Mattiasson B (2009) A capacitive biosensor for detection of staphylococcal enterotoxin B. Anal Bioanal Chem 393: 1539-1544.) Results from the ECD assay are at the lower end of detection for the assays listed in this publication. The excellent performance of the ECD assay is related to using the microarray to identify Ppy deposition conditions that maximized the signal from SEB binding while minimizing the signal from non specific binding.

While distinct in the approach, optimizing Ppy deposition appears similar to but more exact than treatment of polystyrene to produce high protein binding surfaces on beads and plates. The commercial instruments and CMOS microarray offer a broad set of tools for developing protein assays on a compact, high throughput platform that supports both electrochemical and fluorescence detection. In conjunction with the MX300 instrument, Ppy can be deposited on a microarray under optimal conditions for protein adsorption; and multiplex assays can be developed by sequentially depositing Ppy and different proteins. Ppy and protein deposition on electrodes is uniform, and groups of electrodes can be used for each capture protein to provide statistical significance. From a practical standpoint of developing a sensitive and specific assay on a Pt electrode, the microarray can rapidly sort these factors empirically to optimize assay results.

Instrumentation

The ElectraSense microarray, ElectraSense Reader and methodology for ECD have been described previously (Ghindilis A L, Smith M W, Schwarzkopf K R, Roth K M, Peyvan K, et al. (2007) CombiMatrix oligonucleotide arrays: genotyping and gene expression assays employing electrochemical detection. Biosensors & Bioelectronics 22: 1853-1860; Roth K M, Peyvan K, Schwarzkopf K R, Ghindilis A (2006) Electrochemical detection of short DNA oligomer hybridization using the CombiMatrix ElectraSense microarray reader. Electroanalysis 18: 1982-1988.) Each ElectraSense microarray has 12,544 individually addressable electrodes that are connected by CMOS circuitry. Thirteen pogo pads on the side of the array provide electrical contact with instrumentation to support different transducer functions. The Pt working electrode is 44 μm in diameter and is separated by a layer of silicon oxynitride from a Pt counter electrode (grid) that is continuous across the surface of the array. The surface of the working electrode is irregular because of the underlying CMOS circuitry, which connects a via to different lines that create one of six different electrode states, which are V0-Read Line, V1-Ground, V2-Voltage Input, V3-Not Used, NC-Float, NC-Not Used, and Current Source. There is a via that is a read back line. The working electrode is circular with a silicon nitride insulating layer surrounding it. There is a platinum grid counter electrode around the insulating layer.

In an embodiment, a PotentioSense™ Microarray Workstation was used in the analysis of the deposition of Ppy and Ab. This workstation was developed to investigate electrochemical processes on the microarray. The instrument software provides a scripting interface, which enables the user to write a protocol (chip map) that controls whether the instrument addresses electrodes individually or in groups. The state of the electrode(s) can be set to source voltage or current, ground, or disconnected (floating) Similarly, current and voltage can be read from a single electrode or a defined group of electrodes using the software and electronics in the instrument and on the microarray. Direct connections to the microarray are externalized on the PotentioSense so that it will interface with third party instruments; e.g., potentiostat, oscilloscope, wave generator, etc. High tolerance electronics are used in the PotentioSense along with software and hardware feedback routines to generate and measure electrical signals accurately. In addition, the instrument is factory calibrated, and calibration values are saved in the device to ensure accuracy and precision.

In an embodiment, the CombiMatrix MX300 is used and has an automated fluidic handling and electrochemical processing station for the ElectraSense microarray. The MX300 includes an automated fluidic handling system and all of the electronics and software found on the PotentioSense. Using a standard 96-well plate, a user can load any combination of reagents and direct their introduction onto the microarray using a scripting program. This instrument can deposit Ppy and different Abs on different electrodes, and, using a different set of instructions and reagents, it can run an ECD immunoassay to determine antigen (Ag) concentration in one or more samples. In an embodiment for Ppy deposition, the MX-300 was configured with a single chamber that covered the array (12K configuration). In an embodiment for antigen detection, the MX-300 was configured with four separate chambers (4×2K configuration) with 2,000 electrodes in each chamber. This allowed analysis of multiple samples on a single microarray.

Antibody Attachment to Electrodes

A number of approaches were investigated to develop an immunoassay on the microarray that would improve upon the method of using nucleic acid-antibody conjugates as capture elements. Initial studies used different chemistries for immobilizing Ab on spotted arrays. However, spotting created uneven depositions across numerous electrodes, which caused uneven and variable fluorescent and ECD measurements. Subsequent efforts focused on using electropolymerized Ppy deposition to attach (possibly entrap or adsorb) antibodies onto individual electrodes. For each experiment, a chip map was created that directed the application of constant current to groups of 5×5 electrodes on the array, Ppy was electrodeposited applying 1.0 V for 5 s, and murine IgG was selectively adsorbed to the deposited Ppy for 5 min. FIG. 1 shows two images of the 5×5 sectors with and without Ppy and Ab. In the left micrograph, Ppy deposition is clearly present as brown spots isolated on each electrode. The array was treated with Cy5-labeled goat anti-mouse IgG, and the fluorescence image shows that the antibodies were localized only on electrodes with Ppy as shown in the right micrograph.

Figure 2:
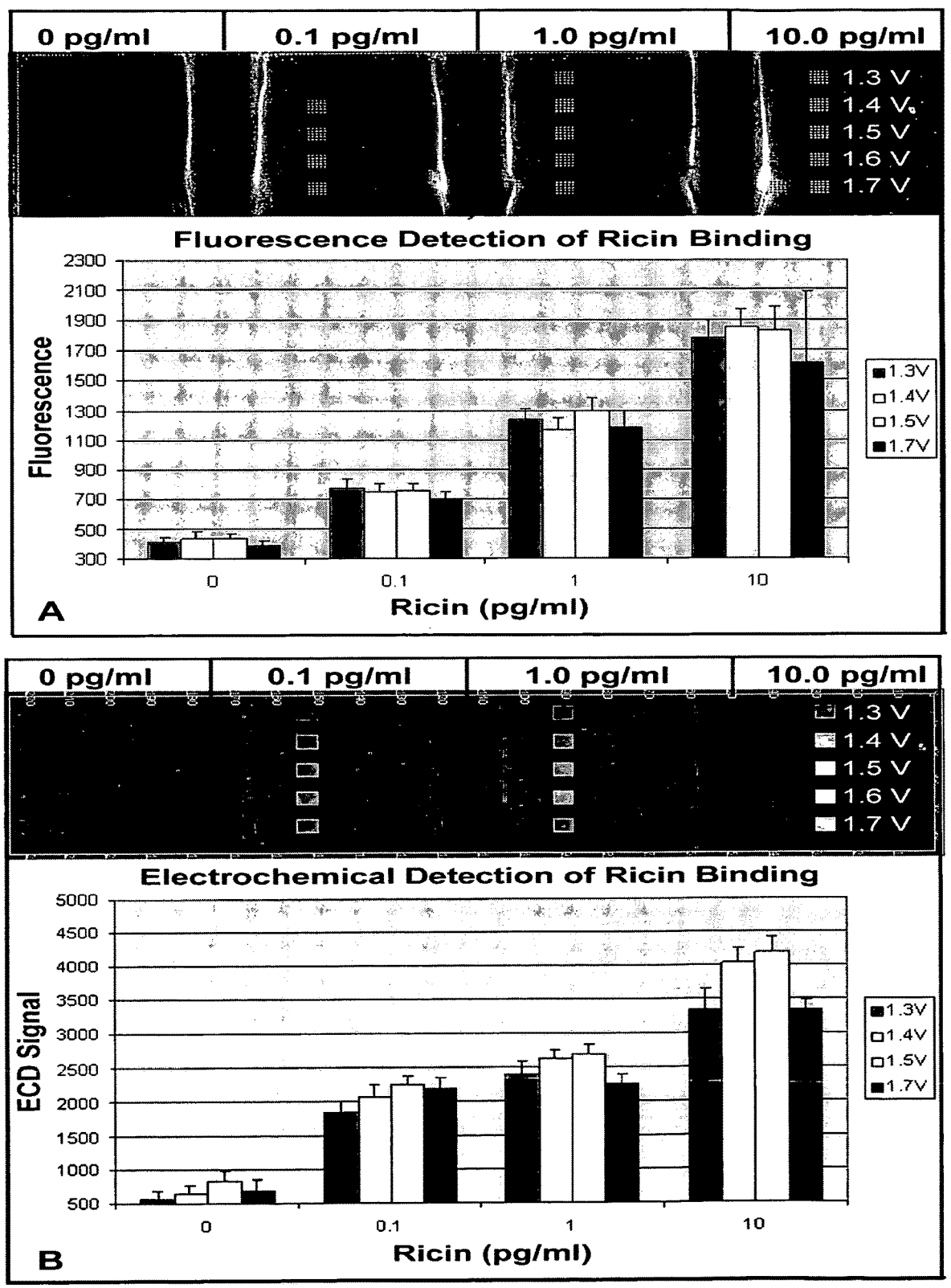
FIG. 2. Detection of ricin binding to murine anti-ricin MAb adsorbed on Ppy deposited at different voltages. Three concentrations of ricin were incubated in different chambers for 1 h and detected with biotin-labeled goat anti-ricin Ab. A) A scanned fluorescence image following incubation with Cy5-SA. B) An ECD pseudo image of the array following incubation with HRP-SA and peroxide/TMB. C) Bar graphs illustrating the quantitative results from the two micro arrays.

To determine whether adsorbed Abs on the array are functional, Ppy was deposited in 5×5 blocks of electrodes and at four different voltages (1.3, 1.4, 1.5, and 1.7 V) for 5 s. Subsequently, anti-ricin monoclonal Ab (MAb) was adsorbed onto the electrodes. Three concentrations of ricin (0.1, 1.0, and 10.0 pg/ml) were tested, and binding was detected using biotinylated goat anti-ricin Ab and HRP-streptavidin (HRP-SA) for ECD. After measurement, the array was washed, and Cy5-streptavidin (Cy5-SA) was applied to the same array for fluorescent detection. FIGS. 2A and 2B illustrate respectively the microarray fluorescence image and the ECD pseudo image that were generated. The bar graphs show that ricin could be detected at 0.1 pg/ml using ECD or fluorescence detection under optimized conditions. In this experiment, increasing the deposition potential to 1.7 V reduced the ECD signals for all concentrations of ricin compared to results using lower deposition voltages; however, this trend was not observed using fluorescence detection.

Optimization of Antibody Attachment

Figure 3:
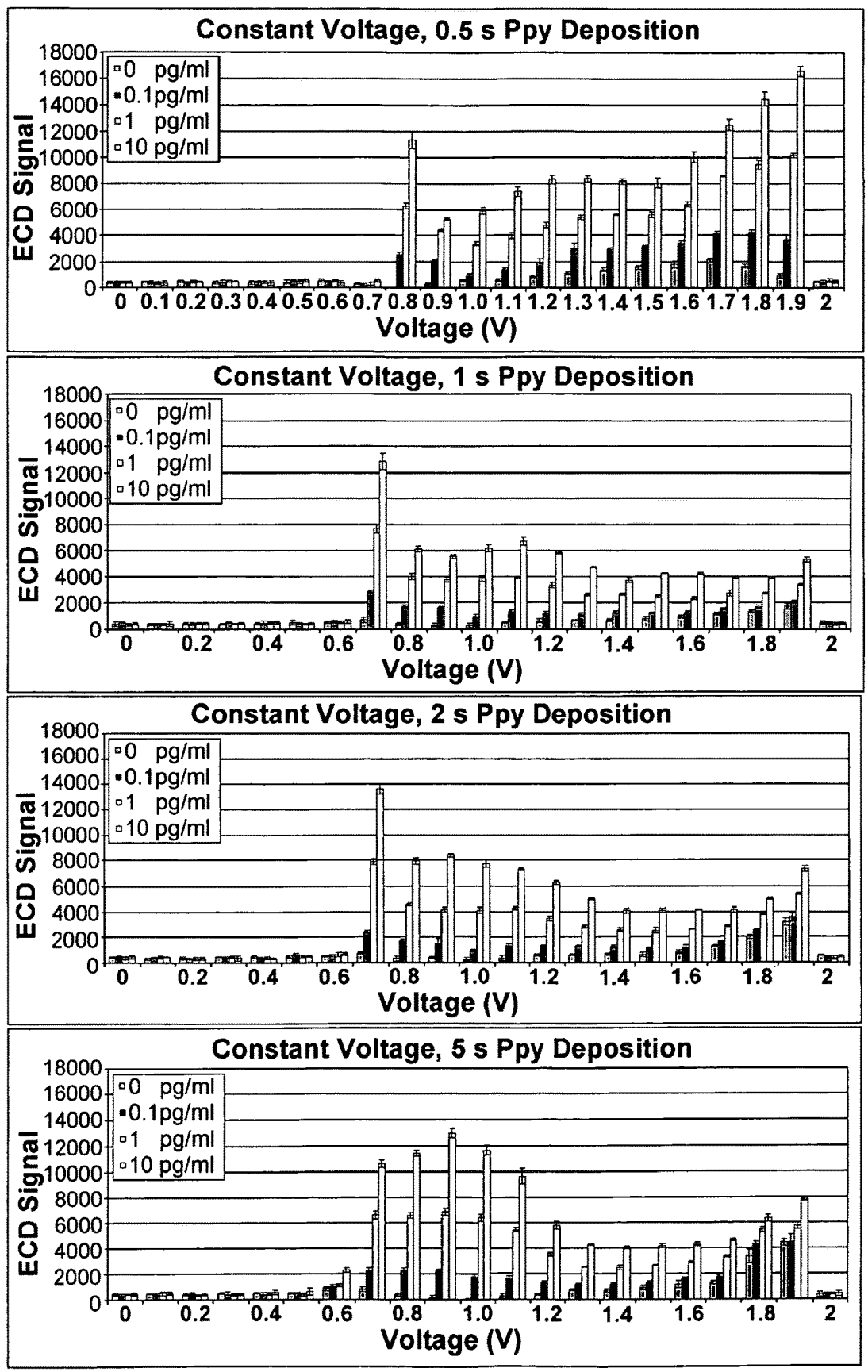
FIG. 3. Electrochemical detection of SEB binding on an array with Ppy deposited using constant voltage. Polypyrrole was deposited using potentials from 0.0 to 2V for 0.5, 1.0, 2.0, or 5.0 s followed by adsorption of anti-SEB MAb. Three concentrations (0.0, 0.1, 1.0 or 10.0 pg/ml) of SEB were incubated in different chambers of a 4-chamber hyb cap, and binding was detected using biotinylated rabbit anti-SEB with HRP-SA.
Figure 4:
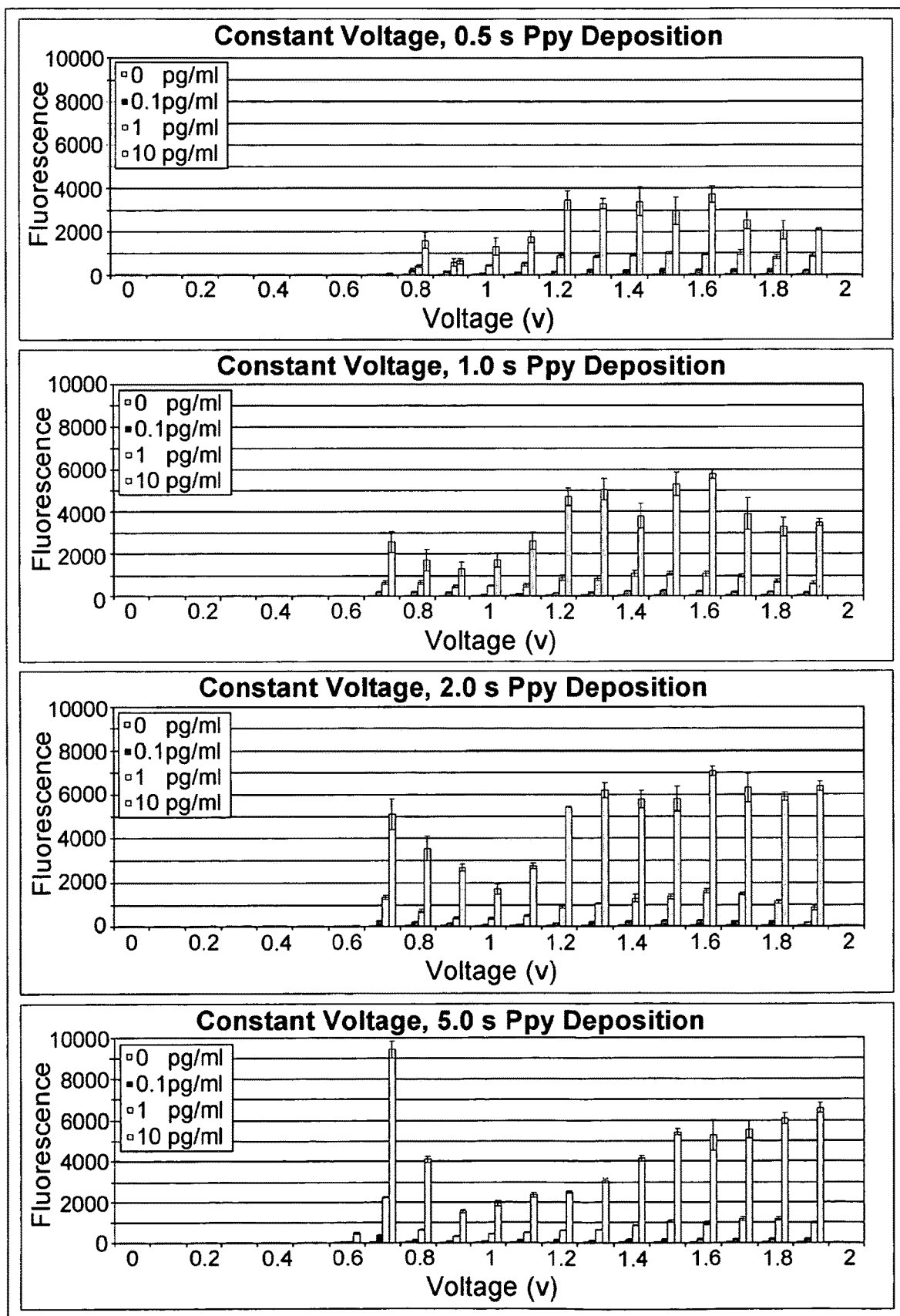
FIG. 4. Fluorescence detection of SEB binding on an array with Ppy deposited using constant voltage. Polypyrrole was deposited using potentials from 0.0 to 2V for 0.5, 1.0, 2.0, or 5.0 s followed by adsorption of anti-SEB MAb. Three concentrations (0.0, 0.1, 1.0 or 10.0 pg/ml) of SEB were incubated in different chambers of a 4-chamber hyb chambers, and binding was detected using biotinylated rabbit anti-SEB with Cy5-SA.
Figure 5:
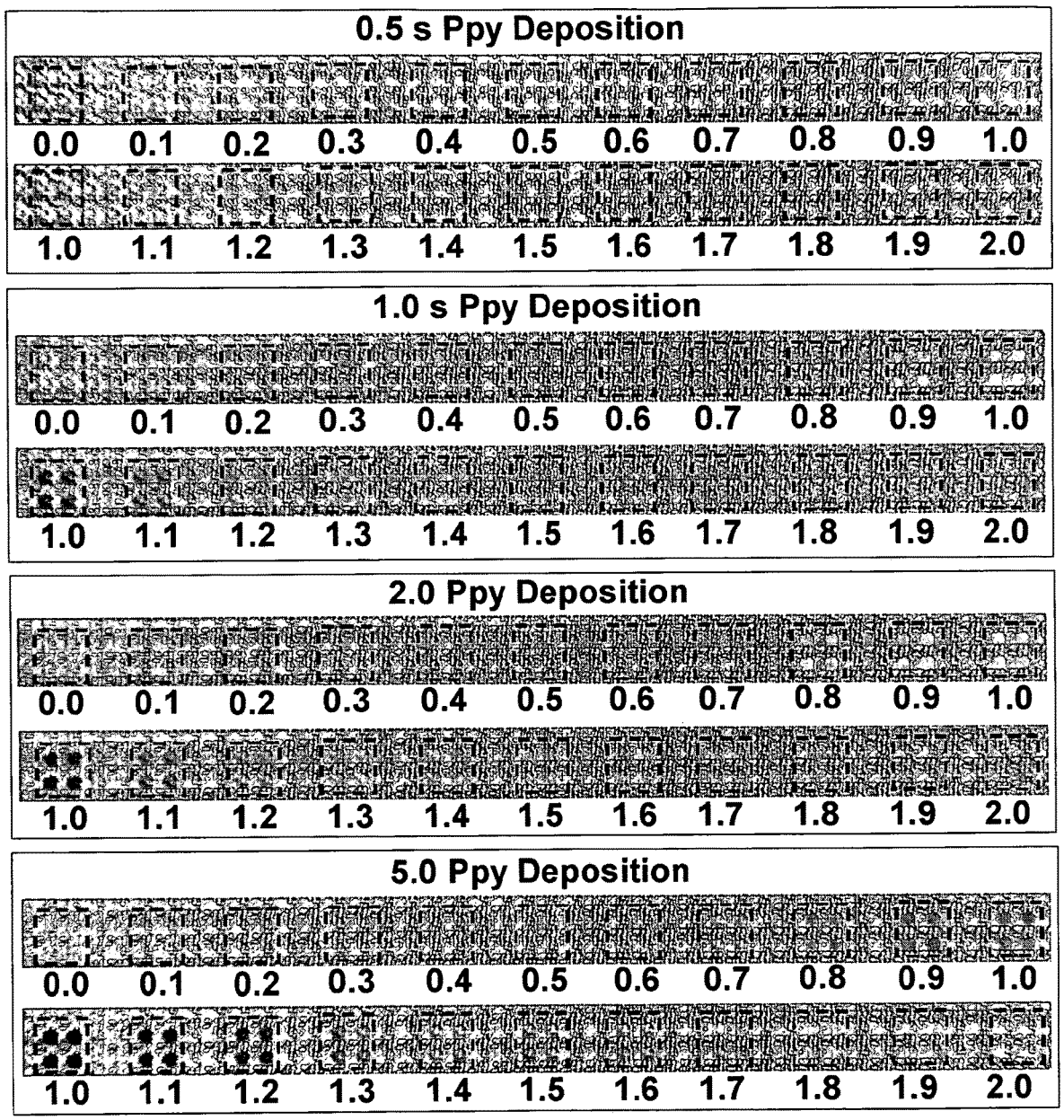
FIG. 5. Composite photomicrograph showing Ppy deposition on 2×2 groups of electrodes using constant voltage. Polypyrrole was deposited for 1.0 s using voltages from 0.0 to 2.0 V in 0.1 V increments, as listed beneath each group.
Figure 6:
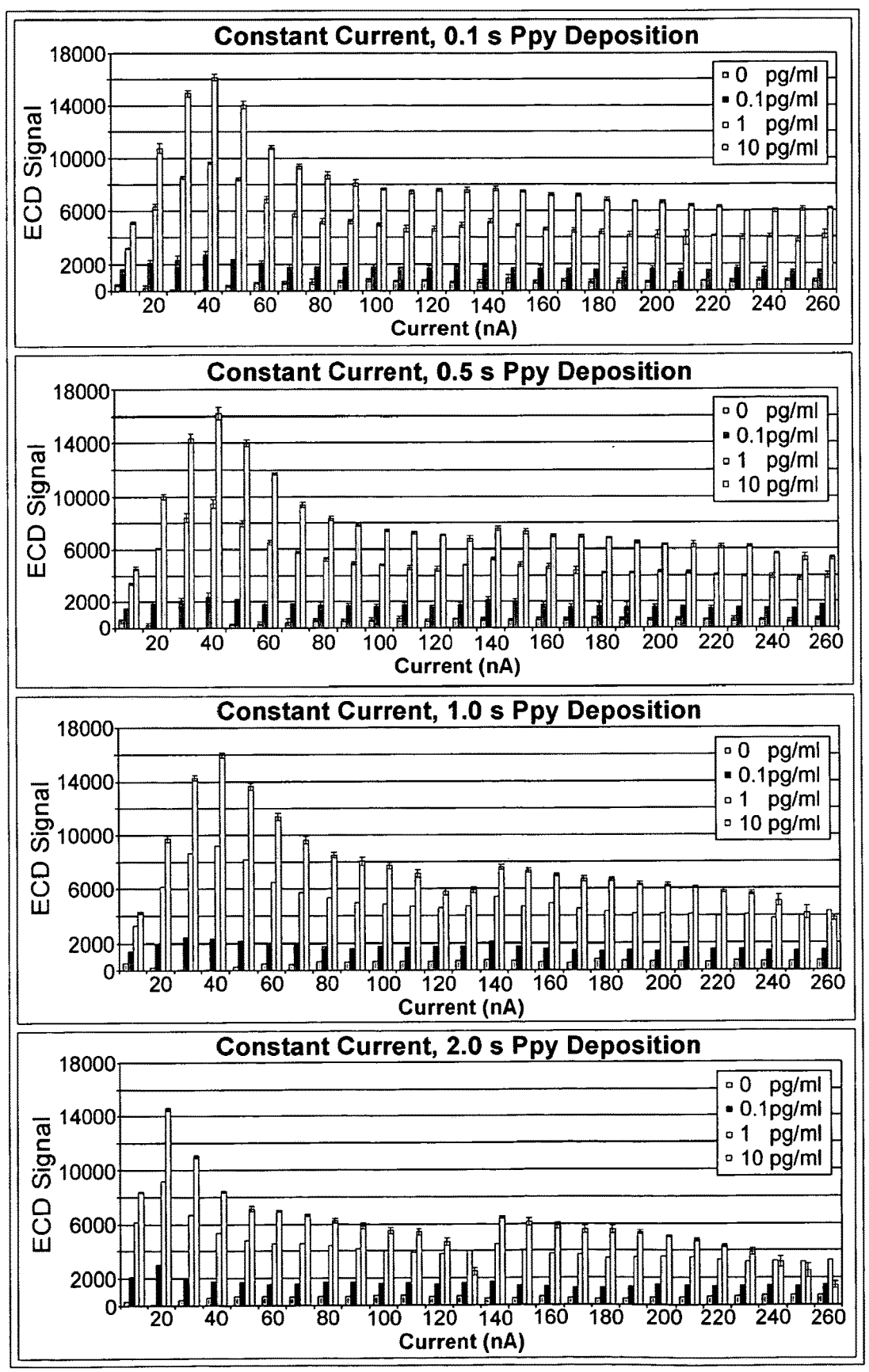
FIG. 6. Electrochemical detection of SEB binding on an array with Ppy deposited using constant current. Polypyrrole was deposited using currents from 10 to 260 nA for four different periods of time (0.1, 0.5, 1.0, and 2.0 s). Three concentrations (0.1, 1.0 or 10.0 pg/ml) of SEB were incubated in different chambers of a 4-chamber hyb cap, and binding was detected using biotinylated rabbit anti-SEB with HRP-SA.
Figure 7:
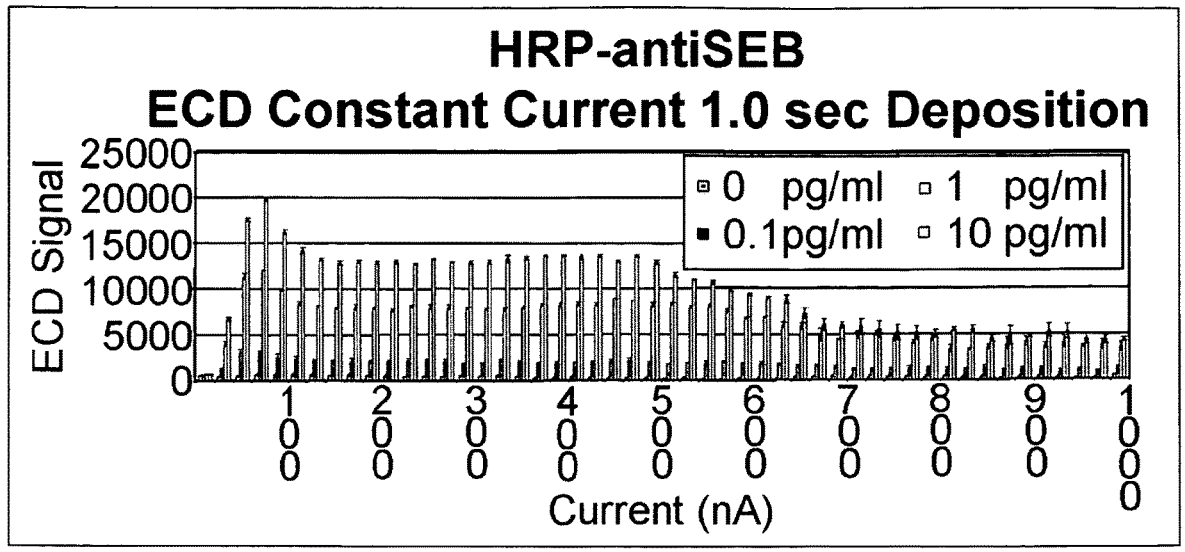
FIG. 7. Electrochemical detection of SEB binding on an array with Ppy deposited using constant current. Polypyrrole was deposited using constant current from 0 to 980 nA for 1.0 s. Three concentrations (0.1, 1.0, and 10.0 pg/ml) of SEB were incubated in different chambers of a 4-chamber hyb cap, and binding was detected using biotinylated rabbit anti-SEB as the secondary Ab and HRP-SA.
Figure 8:
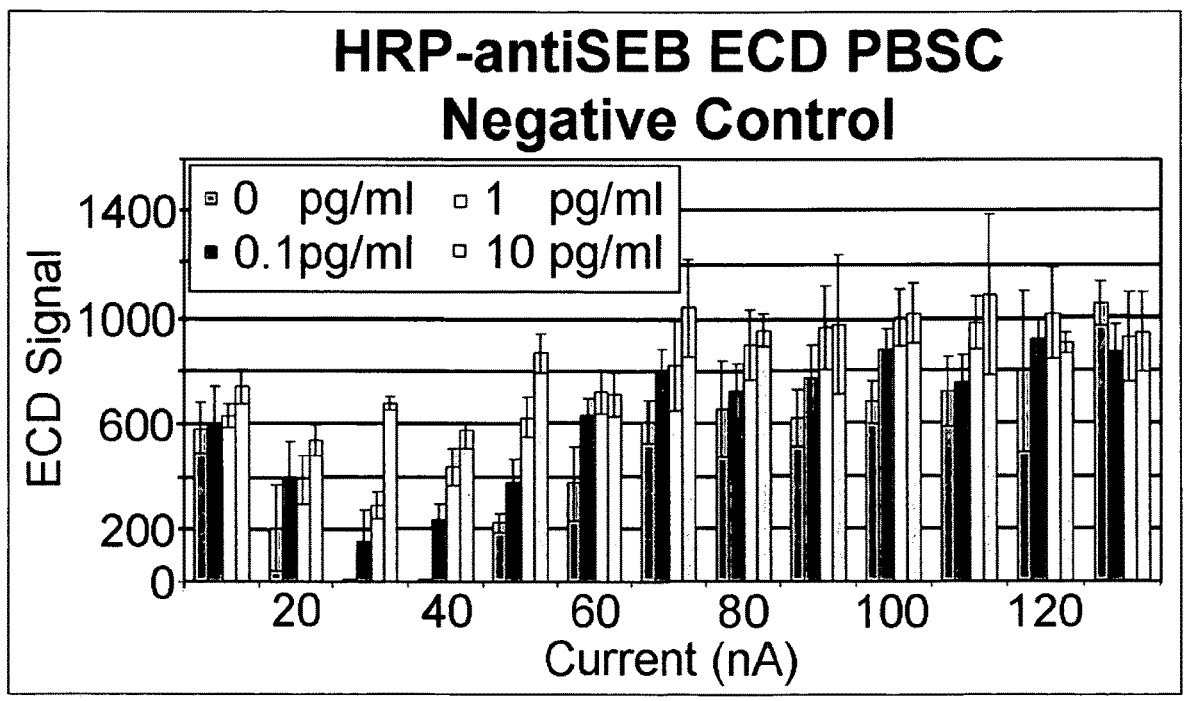
FIG. 8. Electrochemical detection of non-specific binding by SEB. Polypyrrole was deposited for 1 s at increasing currents from 10 to 130 nA and blocked with saturated casein in place of capture Ab. Binding was detected using biotinylated rabbit anti-SEB with HRP-SA.
Figure 9:
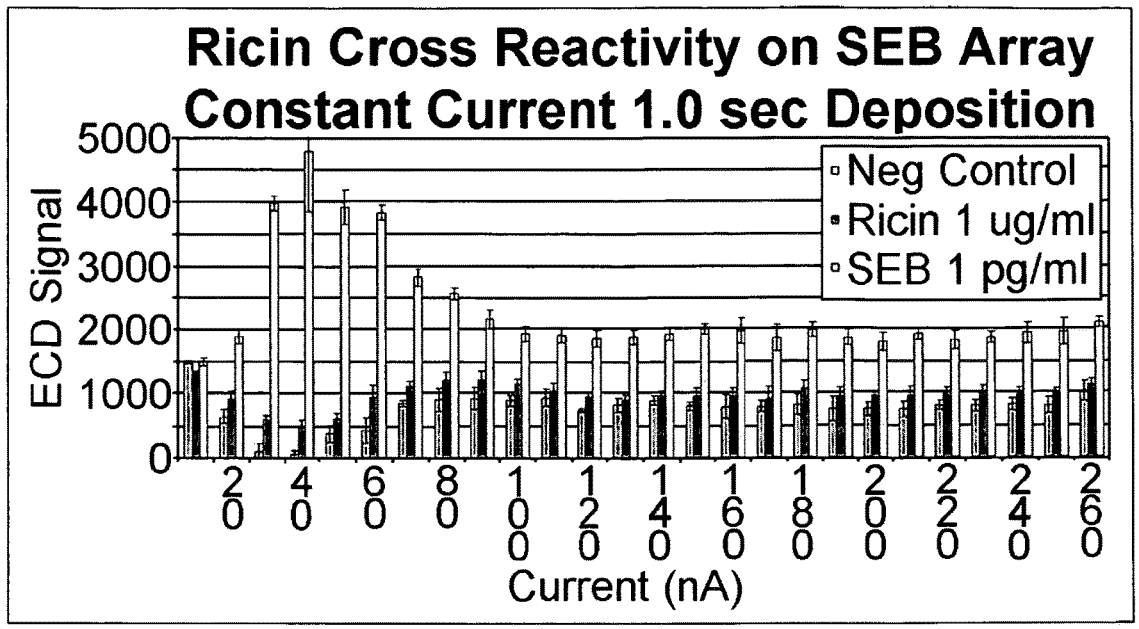
FIG. 9. Electrochemical detection of cross reactivity by ricin with rabbit anti-SEB capture Ab. Polypyrrole was deposited for 1 sec at increasing currents from 10 to 260 nA. Biotinylated rabbit anti-SEB Ab was used to detect SEB and biotinylated goat anti-ricin Ab was used to detect ricin.
Figure 10:
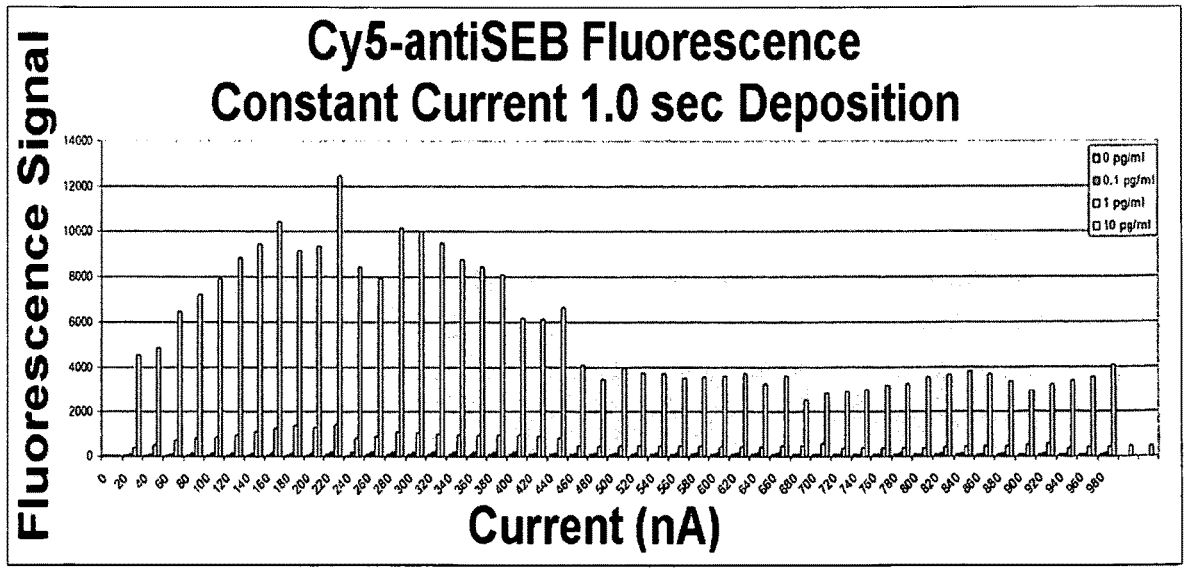
FIG. 10. Fluorescence detection of SEB binding on an array with Ppy deposited using constant current. Polypyrrole was deposited using constant current from 0 to 980 nA for 1.0 s. Three concentrations (0.1, 1.0, and 10.0 pg/ml) of SEB were incubated in different chambers of a 4-chamber hyb cap, and binding was detected using biotinylated rabbit anti-SEB as the secondary Ab and Cy5-SA.
Figure 11:
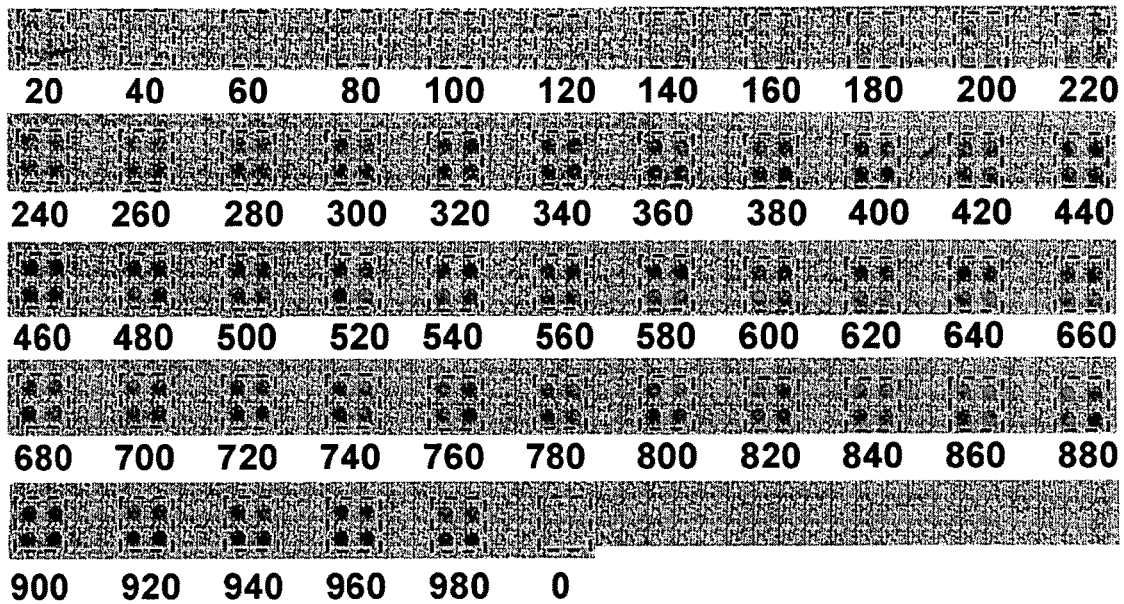
FIG. 11. Composite photomicrograph showing the deposition of Ppy on 2×2 groups of electrodes. Polypyrrole was deposited using constant current (0.0 to 980 nA) for 1.0 s as listed beneath each group.
Figure 12:
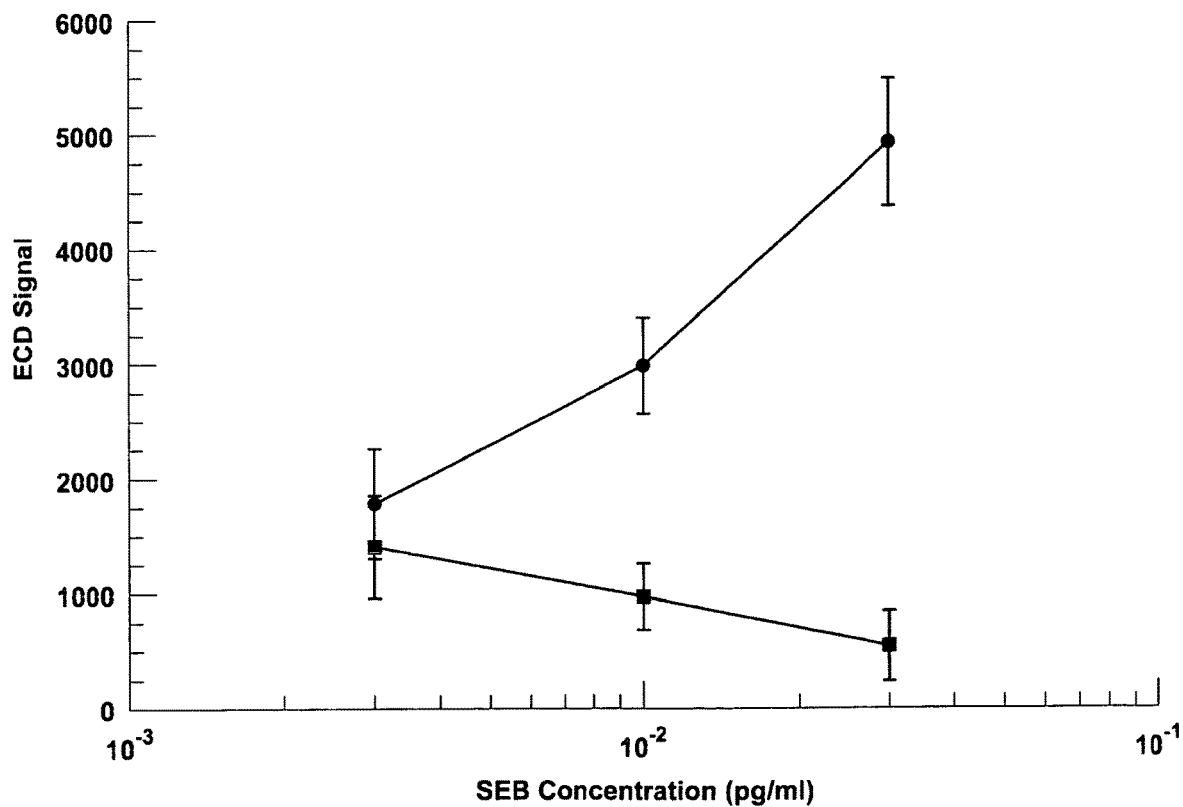
FIG. 12. Determination of the LOD for SEB using ECD. Three concentrations (0.003, 0.01, and 0.03 pg/ml) were incubated on a microarray with either anti-SEB MAb (●-●) or casein (■-■) adsorbed onto Ppy that was deposited at 40 nA for 1 s. SEB binding was detected using biotinylated rabbit anti-SEB Ab and SA-HRP. Background (0 pg/ml SEB) was 1147+−283.
Figure 13:
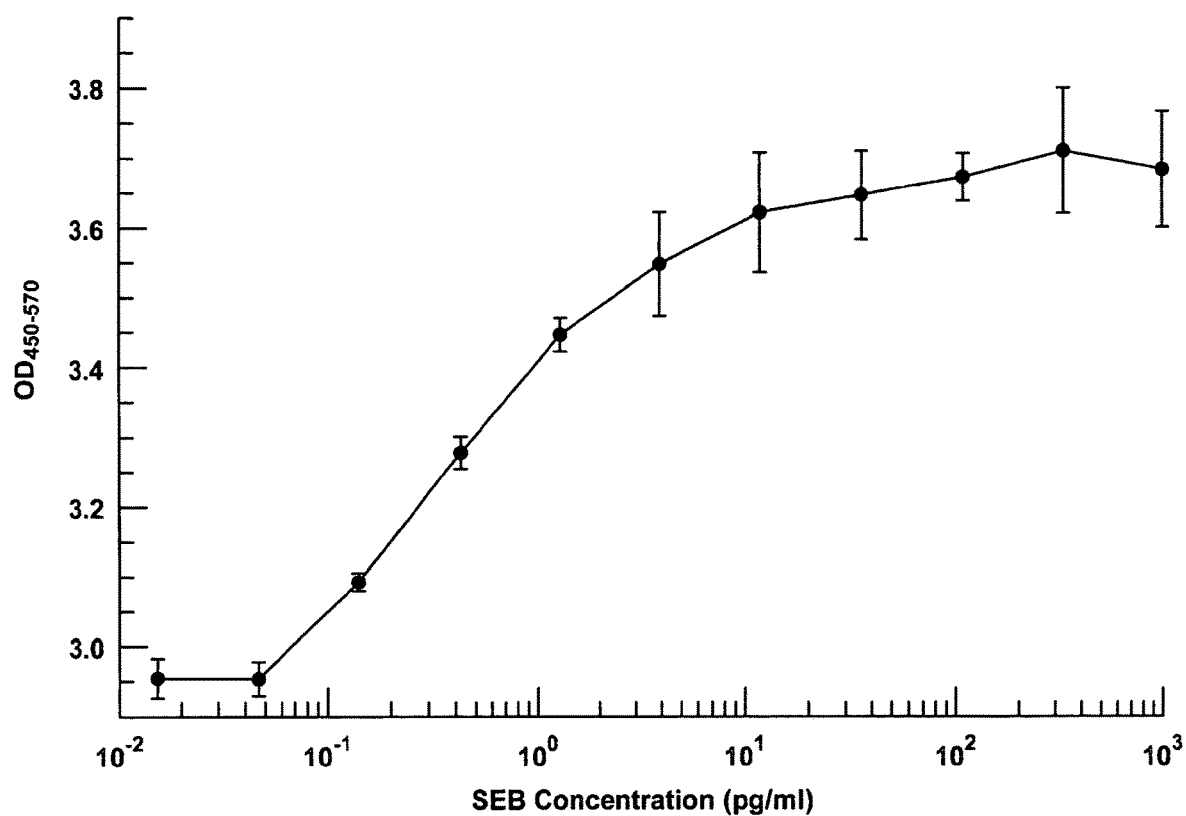
FIG. 13. Determination of the LOD for SEB using a microplate ELISA assay. Different concentrations of SEB were incubated on a microtiter plate with anti-SEB MAb adsorbed onto the surface of each well. SEB binding was detected using biotinylated rabbit anti-SEB Ab and SA-HRP. Background (0 pg/ml SEB) was $OD_{450-570}$ 2.939+−0.026.

To determine the relationship between deposition potential and assay sensitivity, a revised assay was developed using SEB as the target. A chip map was written on the MX300 instrument to create blocks of 2×2 electrodes in four sectors that align with a four-chambered (hyb) cap. Each block had a different set of Ppy deposition conditions based upon voltage (0-2 V in increments of 0.1 V) and time during which voltage was applied (0.5, 1.0, 2.0, and 5.0 sec). Anti-SEB MAb was adsorbed to all blocks of electrodes except for a row of control blocks, which were treated with casein only and served as negative controls. Different concentrations of SEB (none, 0.1 pg/ml, 1.0 pg/ml, and 10.0 pg/ml) were tested on the array followed by incubation with biotinylated rabbit anti-SEB Ab and SA-HRP. FIG. 3 illustrates that significant SEB binding was measured using ECD when the Ppy was deposited between 0.7 and 1.9 V. Time of deposition had little influence on this window of deposition; however, within this window both time and voltage influenced assay sensitivity (signal in the presence of SEB and capture Ab versus control). Better sensitivity was achieved using lower voltages (0.7 to 1.0 V) for a longer period of time (5 s). Higher voltages reduced specific binding and increased non-specific binding.

Because the SEB detection was apparent only when voltages between 0.7 and 1.9 V were applied, the assay was run using Cy5-SA and fluorescence detection to determine if this window was related to the Ab deposited on the Ppy or some electrical properties of the Ppy. FIG. 4 illustrates that, as observed with ECD, SEB was only detected fluorescently on Ppy deposited between 0.7 and 1.9 V. Within this window of deposition, the fluorescence pattern reflecting assay sensitivity was bimodal like the ECD assay but non-specific binding to electrodes treated only with casein (control) was very low. To understand these patterns better, photomicrographs were made of Ppy deposited on the array. FIG. 5 shows the pattern of Ppy deposited on blocks of electrodes for 2 s at 0.0 to 2.0 V. The product was first apparent at 0.7 V, the intensity of the color (increased signal indicated by darker spots) appeared to increase with increasing potential to 1.0 V and it then declined thereafter but was still apparent at 1.9 V.

In an alternative embodiment to constant voltage deposition, Ppy was deposited using constant current. Assay conditions were identical to those described above, except for deposition times (0.1, 0.5, 1.0 and 2.0 s) and current. FIG. 6 illustrates results from an assay where Ppy was deposited using 10-260 nA. The best sensitivity, as measured by ECD, was obtained when a deposition current of 40 n A was applied for 0.1, 0.5 or 1.0 s. When current was applied for 2.0 s, the curve moved to the left, and the best activity was observed with a lower deposition voltage of 20 nA. FIG. 7 illustrates results from a similar assay in which a broader range of currents (0-980 nA) was applied for 1 s for Ppy deposition. The ECD signal increased to a peak at 60 nA and then declined with plateaus at 120-460 nA and 660-920 nA. FIG. 8 illustrates SEB binding to negative control electrodes that were blocked with casein. The lowest non specific binding to the electrodes was observed when Ppy was deposited at 20-40 nA for 1 s. FIG. 9 illustrates cross reactivity of the SEB assay with ricin in excess. As with the negative control, ricin binding was minimal when the Ppy was deposited at 30-40 nA for 1 s but increased on Ppy deposited at lower and higher currents. That ricin binding increased along with the negative control (no Ag) suggests that other components in the assay (e.g., biotinylated secondary Ab or SA-HRP) may have contributed to the non-specific signal.

This assay was repeated using fluorescence detection, and FIG. 10 illustrates peak detection on Ppy deposited at 220 nA for 1.0 s, after which the fluorescence signal decreases with increasing deposition currents. In addition, non-specific binding to electrodes treated only with casein (control) was minimal throughout the range of currents used for Ppy deposition. The pattern of colored Ppy was examined microscopically, and FIG. 11 illustrates that colored product was apparent on electrodes after a 1 sec 160 nA deposition. The intensity of the colored product increased and appeared to reach a plateau thereafter but did not demonstrate the loss of color intensity that was observed with constant voltage deposition.

SEB Immunoassay Assay Performance Comparison

To determine a LOD for the enzyme-enhanced ECD assay, lower concentrations of SEB were tested using a new version of the ElectraSense reader with improved electronics that reduce electronic noise and increase ECD signals. FIG. 12 illustrates that the assay was able to detect 0.01 pg/ml in PBSC but not at 0.003 pg/ml. A standard ELISA microwell plate assay was developed around the same capture and secondary Abs, and FIG. 13 illustrates that this assay detected SEB at 0.15 pg/ml but not at 0.05 pg/ml indicating that the ECD assay was at least an order of magnitude more sensitive than the ELISA plate assay.

SEB Immunoassay Reagents

For development of the SEB immunoassay in an embodiment, the antigen and antibodies (rabbit anti-staph entertoxin B and anti-staph entertoxin B MAb) were purchased the Critical Reagent Program (Critical Reagent Program, Aberdeen Proving Ground, Md.). Ricin was purchased from Sigma-Aldrich (Sigma-Aldrich, St. Louis, Mo.), and ricin MAb and goat anti-ricin Ab were purchased from the Critical Reagent Program as a secondary (reporter) Ab. The SEB and ricin antibody pairs were evaluated for their functionality as capture and secondary antibodies, and the best results were obtained using the MAb as the capture Ab and the polyclonal Ab as reporters. Both secondary Abs were labeled with EZ-link Sulfo-NHS-LC-Biotin (Thermo Fisher Scientific, Rockford, Ill.). The protein blocking solution (PBSC) was prepared by mixing three grams of casein (Casein from Bovine Milk, Technical Grade, Sigma-Aldrich) in one liter of phosphate buffered saline (PBS, pH7.2) with stirring for 1-2 h. The suspension was refrigerated overnight and allowed to filter under gravity flow through a 0.22 μm filter (Steritop-GP, Millipore, Billerica, Mass.) at 4° C. for 24 h. Pyrrole (Sigma-Aldrich) was distilled and stored under argon in sealed glass ampoules at 4° C. and protected from the light. The 0.1 M working solution of pyrrole was prepared by diluting the distilled reagent in 0.1M dibasic sodium sulfate (Sigma-Aldrich) in water immediately prior to use. Photomicrographs of Ppy deposition on the microarray were made using an Olympus BX60 microscope with epi illumination (Center Valley, Pa.).

Deposition of Polypyrrole and Capture Antibody—SEB Immunoassay

To deposit the anti-SEB MAb on individual electrodes in an embodiment, a chip map was created for the PotentioSense instrument by designating through the software which electrodes were to be addressed, the voltage or current to be applied, and the time of application. The chip map created 4 replicated areas on the array that corresponded to the four chambers of a plastic hyb cap (ElectraSense Hybridization Cap, 4×2K, CombiMatrix Corp, Mukilteo, Wash.). Within each area, 2×2 or 5×5 blocks of electrodes were ganged so that they received the same voltage or current for the same period of time. For manual deposition, a single-chambered hyb cap (ElectraSense Hybridization Cap, 12K) was mounted on the array using a clamp (CustomArray® Clamp for 4×2 & 12K) that fits into the PotentioSense. For automated processing, an MX300 with a single chamber (12K configuration) was used. To prevent non specific binding, the array was treated with PBSC for 5 min, washed three times with PBS containing 0.1% Tween 20 (PBST), three times with PBS and three times with 0.1M dibasic sodium sulfate prior to adding pyrrole for electrodeposition. After Ppy deposition, the array was washed twice with PBS; and capture Abs, diluted in PBS, were added for 15 min at 25° C. The array was washed three times with PBSC and blocked with the same for 2-5 mins. For fixing a second capture Ab on the array, all steps starting from the initial block with PBSC were repeated. After Ab deposition, the microarray was blocked with PBSC for 1 h, treated with Post Coating Buffer (ALerCHEK, Portland, Me.), spin coated, and stored at 4° C.

Microarray Immunoassay

In an embodiment, microarray immunoassays were done manually so that results from experiments using ECD and fluorescence detection were processed in the same manner. For an assay, the microarray was fitted with a four-chamber hyb cap and washed with PBSC before 40 µl of Ag in PBSC or PBSC (control) was loaded into each chamber. Following a 1 hr incubation at 25° C., the chambers were washed five times with PBSC; and biotin-labeled secondary Ab (diluted to 2 µg/ml in PBSC) was added for a 1 hr incubation at 25° C. After washing thrice with PBSC, the four-chambered hyb cap was removed and replaced with at single chambered hyb cap, and the array was washed three more times. For fluorescence detection, CY5®-streptavidin (GE Healthcare, Amersham Biosciences, Piscataway, N.J.) was added for 1 h, washed 5 times in PBSC and twice in PBS and scanned on a GenePix 4000B (Axon Instruments, Molecular Devices, Sunnyvale, Calif.). For ECD, microarrays were incubated for 30 min with Poly-80-HRP Streptavidin (Fitzgerald Industries International, Acton, Mass.) diluted 1:1000 in PBSC. Arrays were washed four times with PBSC, once with PBS, and twice with pH 4 Conductivity Buffer Substrate (BioFX, Owings Mills, Md.). TMB Conductivity 1 Component HRP Microwell Substrate (BioFX) was added to the array, and it was scanned immediately with an ElectraSense microarray reader (CombiMatrix). Data were quantified using Microarray Imager or ElectraSense software (CombiMatrix) for fluorescent scans or ECD respectively.

Microwell ELISA Comparison Assay

Anti-SEB MAb was diluted 1:500 in 0.5 M sodium carbonate-bicarbonate pH 9.6 buffer (Sigma) and 25 µl of the solution was added to each well of a 96-well plate (NUNC Immuno MicroWell 96-Well Plate, Thermo Fisher Scientific). The plate was covered and incubated at 4° C. overnight. Each well was washed five times with 200 µl of PBST and blocked with 1×ELISA Diluent Solution (eBioscience, San Diego, Calif.) for 2 h at 25° C. with agitation. An SEB solution (1000 pg/ml) was prepared in 1× Diluent Solution and serially diluted 1:3 the same to a lowest concentration of 0.015 pg/ml. Each concentration was added to 3 wells, and the plate was incubated 1 h at 25° C. with agitation. After five washes with PBST, each well received 50 µl of biotinylated rabbit anti-SEB Ab, diluted 1:1000 in 1× Assay Diluent; and the plate was incubated overnight at 4° C. For detection, the plate was washed five times with PBST, 100 µl of 1×TMB Substrate Solution (eBioscience) was added, and the plate was incubated at 25° C. for 15 min with agitation. After this time, 50 µl of Stop Solution (eBioScience) was added to all wells, and the plate was read at 450 nm and 570 nm on a SPECTRAmax PLUS 384 microplate reader (Molecular Devices, Sunnyvale, Calif.). For data analysis the $OD_{570nm}$ was subtracted from the $OD_{450nm}$.

High Sensitivity Immunoassay on a Microarray of Serially-Attached Preformed Unmodified Biomolecules In an embodiment, different types of proteins are serially attached to electropolymerized polypyrrole on microelectrodes of an array of microelectrodes to make a microarray of proteins that have not been chemically modified or functionalized in contrast to the functionalized proteins of conventional ELISA. The array is created by directed patterning of proteins on the microarray via pyrrole electropolymerization followed by protein adsorption.

In an embodiment, the unmodified proteins attach (adsorb or by some other mechanism) to the electropolymerized polypyrrole in a very short amount of time. In an embodiment, the surface of a each electrode is platinum, upon which the pyrrole is polymerized. Other electrode surfaces can be used including gold and iridium. In an embodiment, proteins and/or antibodies can be blocked from attaching to the polypyrrole by exposing the microarray to the protein-blocking agent Casein. In an embodiment, the exposing is about 1 minute or less. Other incubation times may be used to block the microarray. In an embodiment, the relatively fast rate of attachment of proteins or antibodies to the polypyrrole is combined with the relatively fast rate of blocking with Casein and with the ability of the microarray to direct polypyrrole polymerization to an individual electrode, or group of electrodes, provide a method to serially pattern a microarray with different proteins and/or antibodies resulting in a protein and/or antibody array. In an embodiment, the proteins or antibodies do not require functionalization in order to direct their attachment, so any antibody or protein, regardless of tagging, can be used.

In an embodiment, a functional ELISA type assay is made on the microarray of microelectrodes, wherein antibodies are attached and then capture an antigen and subsequently detected with a tagged antibody to that antigen (Classic ELISA sandwich assay). In an embodiment, Ricin toxin is detected using this ELISA type assay at as little as 100 fg/mL. In another embodiment, the protein Ricin is attached to polypyrrole and detected using a fluorescently labeled antibody. In another embodiment, Horseradish peroxidase is attached to polypyrrole, and its functionality verified via electrochemical detection. In an embodiment, the protein types attached to the polypyrrole to make a microarray include antibodies, enzyme, and general cellular proteins (Ricin).

Serial Attachment of Proteins on 12K CombiMatrix Microarray

In an embodiment, a method for serial construction of a protein microarray comprises: (a) blocking a microarray with a blocking protein, wherein the blocking protein is Casein or Bovine Calf Serum or a combination thereof; (b) washing the microarray to remove the blocking solution, wherein the step of washing comprises washing three times with PBS/Tween, three times with PBS, and three times with the electrolyte used for the polymerization of pyrrole; (c) electropolymerizing pyrrole for 5 seconds at 1.5 V in Sodium Phosphate on an electrode or set of electrodes that have been predetermined; (d) washing the microarray 3 times with PBS; (e) diluting a protein solution to about 1 µg/ml; (f) exposing the microarray to the protein solution for about 5 to 30 minutes; (g) washing the microarray three times with PBS/tween; (h) blocking the microarray with a blocking solution, wherein the blocking solution is saturated Casein and the time of blocking is about 2-5 minutes; and (i) repeating steps (b) through (h) for each protein to be attached to the microarray.

The voltage will change depending upon which electrolyte is used for the electropolymerization. In an embodiment, concentration of protein is less than 1 µg/ml concentration. Generally, the more concentrated the protein solution, the higher level of binding to polypyrrole in a shorter amount of time. Incubate on chip for 5-30 minutes at room temperature.

There are many parameters that have an effect on the pyrrole deposition/polymerization. Some of these include the following: the electrolyte, the crystallographic structure of the underlying electrode, how the electrode is cleaned, the speed and the potential or current during the deposition, surface area of deposition (# of electrodes on with constant Voltage), concentration of the monomer, and pH of the solution. In an embodiment, pyrrole is deposited/polymerized in a 5×5 pattern of electrodes using SDS as the electrolyte. The electrodes become dark with the deposition of polypyrrole (FIG. 1A).

Antibody Adsorption and Detection

In an embodiment, protein attachment/adsorption was performed with antibodies. In an embodiment, Anti-Ricin monoclonal mouse antibody is adsorbed/bound on polypyrrole deposited in a 5×5 electrode pattern. The antibody was fluorescently detected on the polymer using an Anti-Mouse IgG developed in Goat that was labeled with cy5 dye (FIG. 1B). Once it was observed that antibodies could be detected on the surface of the polypyrrole, the antibodies were then tested for functionality.

Functional ELISA Type Assay

Figure 14:
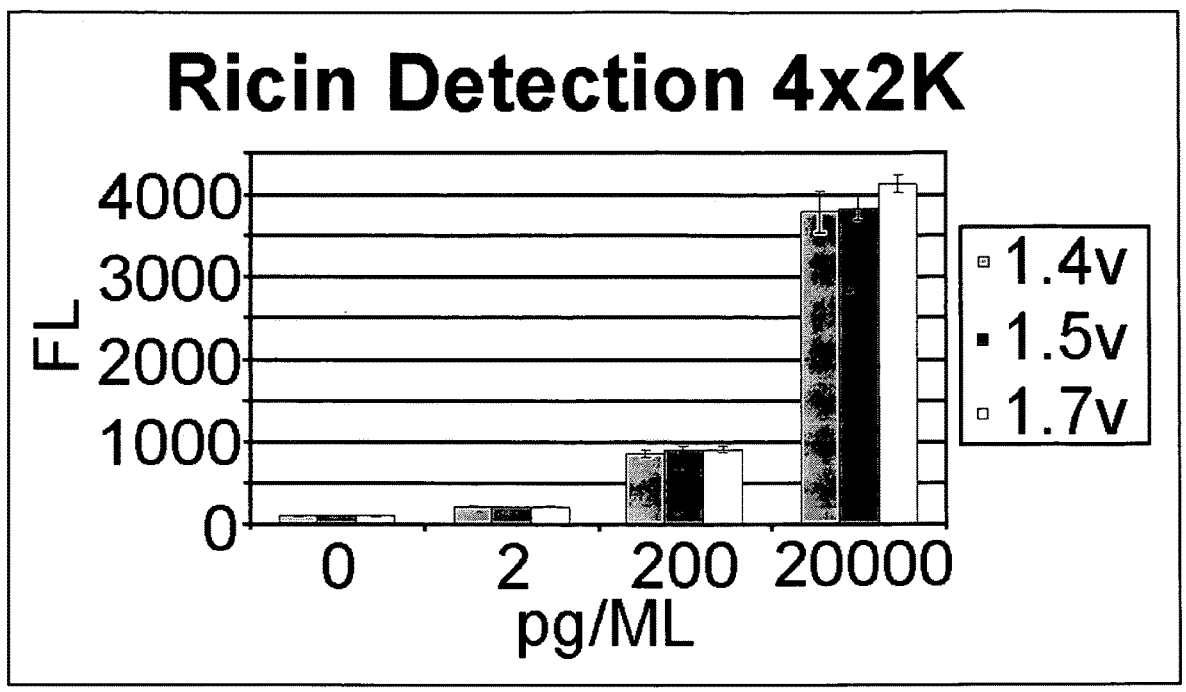
FIG. 14 A graph that shows fluorescence response of the capture of Ricin at a 2 pg/mL.

In an embodiment, Ricin was captured using the adsorbed antibodies and detected using the CombiMatrix electrochemical detection method. FIG. 14 shows the capture of Ricin fluorescently at a 2 pg/mL. Briefly, rabbit Anti-Ricin antibody was adsorbed on the polymer deposited at 1.4, 1.5, and 1.7 volts in each quadrant of a 4×2K CombiMatrix array. Ricin was incubated for one hour at 0, 2, 200, and 20,000 pg/mL in separate quadrant of the 4×2K antibody array for one hour. Ricin capture was detected with biotinylated goat anti-Ricin antibody and Cy5 labeled Streptavidin. Results are detailed in the FIG. 14 and clearly show detection of Ricin at 2 pg/mL above background.

Lower Limits of Detection

Figure 15:
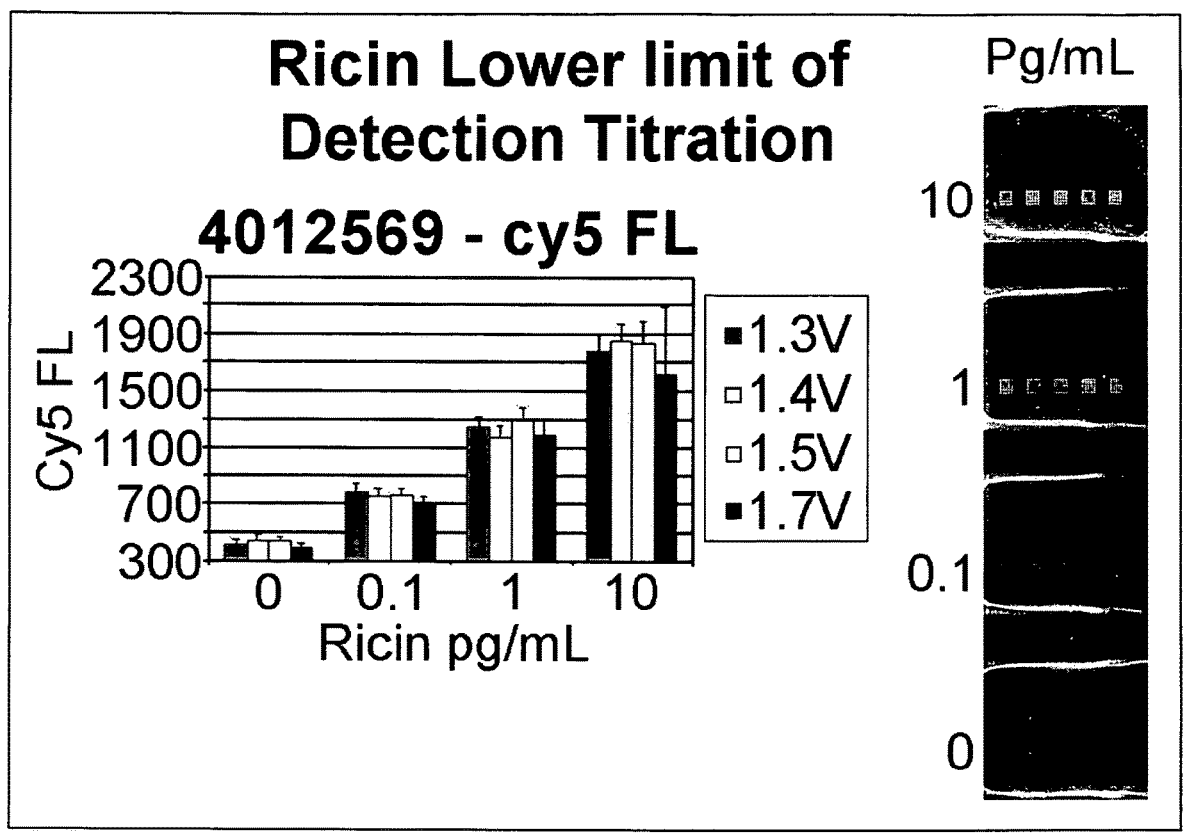
FIG. 15. A graph that shows detection of Ricin at 0.1 pg/mL above background.

To further explore the lower limits of detection of this system, 4×2K arrays (CombiMatrix CustomArray Microarray 12 k) were constructed with anti-ricin antibody as above. Ricin was incubated for 1.5 hrs at 0, 0.1, 1, and 10 pg/mL. Ricin capture was detected with biotinylated anti-Ricin Antibody and cy5 labeled Streptavidin. Results are detailed in FIG. 15 and clearly show detection of Ricin at 0.1 pg/mL above background.

Verification Test

An additional CMOS microarray was tested with the results shown in FIG. 16, which shows 0.1 pg/mL detection of Ricin. This chip was further incubated with biotinylated anti-SA antibody followed by SA-HRP and electrochemical detection using a COMBIMATRIX ELECTRASENSE® detector and standard protocol. The results mirror the Fluorescent detection, also shown in FIG. 16.

Attachment/Adsorption of Ricin

In another embodiment, proteins other than antibodies were tested for adsorption/binding to the polypyrrole. The protein ricin was tested to adsorb/bind to the polypyrrole. Ricin was bound on polypyrrole deposited at 1.0, 1.3, 1.4, 1.5, and 1.7V at 10 µg/ml, 10 ng/mL, and 10 pg/ml concentrations serially for 10 minutes each. This adsorption pattern was repeated in each sector of a 4×2 k microarray. The Ricin was detected using 4 different concentrations of biotinylated goat anti-ricin antibody: 20 µg/mL, 20 ng/mL, 20 pg/mL, and a 0 concentration control, separately in the four chambers of the 4×2 k chip. The results showed positive binding for Ricin to the polypyrrole deposited on the chip as shown in FIG. 17.

Attachment/Adsorption of HRP

Figure 18:
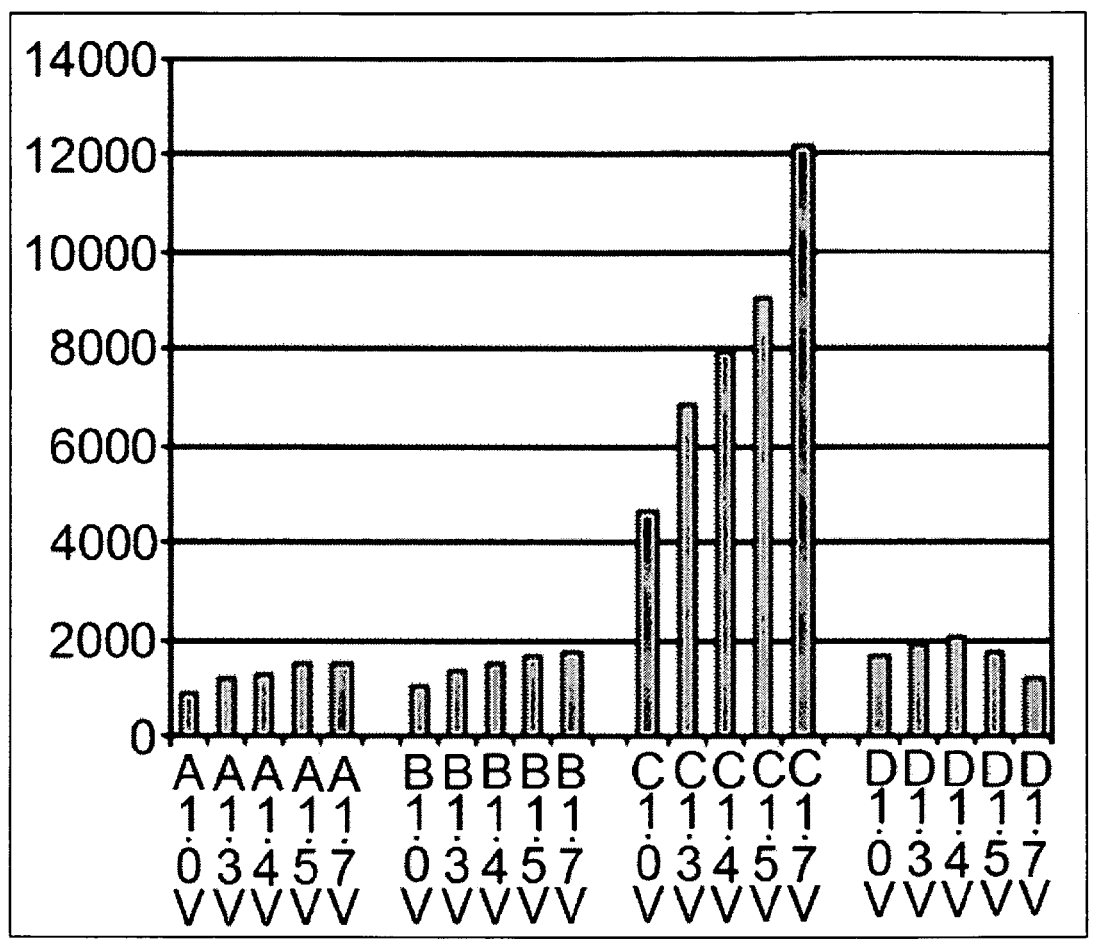
FIG. 18. A graph and image that shows adsorption of functional HRP to the polypyrrole deposited on the electrodes of the microarray.
Figure 18:
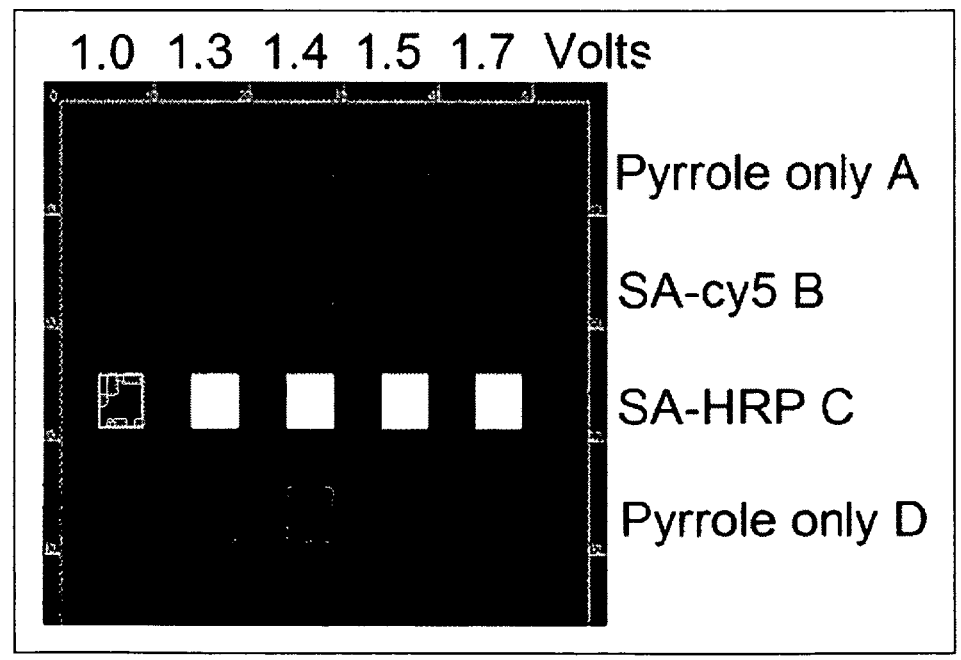

The enzyme horseradish peroxidase (HRP) was tested for binding to polypyrrole deposited on the chip. Polypyrrole was deposited on the chip in 5×5 patterns at 1.0, 1.3, 1.4, 1.5, and 1.7V in row across the chip. After one series of depositions either Streptavidin labeled with Cy5, Streptavidin conjugated to HRP, and no protein controls were adsorbed serially to the pyrrole deposition series. The adsorption of HRP was detected by using the standard ECD detection protocol for the ElectraSense Reader, basically by detecting HRP oxidized TMB via reduction of this TMB at the surface of the electrode. FIG. 18 shows adsorption of functional HRP to the deposited polypyrrole.

Microarray of Serially-Attached Pre-Formed Oligonucleotides

Commercially synthesized DNA probes were attached to an electropolymerized polypyrrole (Ppy) coating on microelectrodes of a microarray of microelectrodes. Hybridization was measured using a biotinylated target oligonucleotide and either Cy5-streptavidin and fluorescence detection or horseradish peroxidase-streptavidin and enzyme-enhanced electrochemical detection. Detection efficiencies were optimized by varying the deposition of the Ppy, the terminal groups on the DNA probes, and other factors that impacted fluorescence quenching and electrical conductivity. Optimized results were compared against those obtained using a microarray with the same DNA sequences synthesized in situ. Immobilized probes produced higher fluorescence signals, possibly by providing a greater stand off between the Cy5 on the target oligonucleotide and the quenching effects of the Ppy and the platinum electrode.

In an embodiment, the 12K microarray was used to make a DNA microarray with electropolymerized Ppy to immobilize different preformed DNA oligonucleotides on individual electrodes. Hybridization was measured using ECD and fluorescence detection on the same platform. Detection efficiencies were optimized by varying the deposition of the Ppy, the terminal groups on the DNA probes, and other factors that impacted on fluorescence quenching and electrical conductivity. Optimized results were compared against those obtained using a microarray with the same DNA sequences synthesized in situ. Immobilized probes produced higher fluorescence signals, possibly by providing a greater stand off between the Cy5 on the target oligonucleotide and the quenching effects of the Ppy and the platinum electrode.

Reagents for Microarray for Preformed Oligonucleotides

Biotinylated oligonucleotide and DNA probes were purchased from Integrated DNA Technologies (Coralville, Iowa). The sequence of the labeled DNA target is 5'-biotin TGC-TTC-TGT-ACG-TTG-TAC-CCA (SEQ ID NO:1), the sequence for the complementary DNA probe is 5'-TGG-GTA-CAA-CGT-ACA-GAA-GCA (SEQ ID NO:2), the sequence of the non complementary DNA probe is 5'-CAA-TAG-CTC-CTG-CTA-CAA-ATG-C(SEQ ID NO:3). Probes were labeled at their 5'-ends with an amine, a disulfide, or a 20 T-linker with an amine. Prior to immobilization on the Ppy, the disulfide DNA was diluted in phosphate buffered saline (PBS) to 0.40 mg/mL and mixed with an equal volume of Immobilized TCEP Disulfide Reducing Gel in PBS (Thermo Fisher Scientific, Rockford, Ill.). The mixture was shaken at 25° C. for 1 h. Following low speed centrifugation, the supernatant was recovered; and the gel was washed once with PBS, which was pooled with the original supernatant to yield a final DNA concentration of 0.20 mg/mL. The thiol-terminated DNA was used immediately to prevent reformation of disulfide bonds. The protein blocking solution (PBSC) and pyrrole were prepared as described previously herein. Propanolamine, cysteine, and thioglycolic acid (Sigma-Aldrich, St. Louis, Mo.) blocking solutions were prepared by suspending each in PBS (pH 7.4) to a concentration of 1.0 M.

Immobilization of DNA Probes on Individual Electrodes

In an embodiment, fluorescence detection and ECD is used on the same experimental platform. Fluorescence detection relies on the measurement of emitted photons resulting from the stimulation of a fluorescent molecule by a high energy light source (e.g., laser). Detection of the emitted light at each electrode (feature) on the array requires an instrument with a stable optical system, detector, and software to create a microarray image. Enzyme-enhanced electrochemical detection uses a redox molecule and substrates to produce electrons that are measured through the electrode, the CMOS circuitry of the array and computer software. Compared with a fluorescent microarray scanner, ECD detectors are much simpler, smaller, more robust, and less expensive. However, fluorescent scanners are widely used because they can accommodate different microarray platforms.

In an embodiment for ECD, hybridization signals were improved when a thin layer of Ppy was applied (30 nA for 1 sec). In an embodiment for fluorescence, detection is improve using a thicker layer, where higher hybridization signals are obtained (260 nA for 1 sec). While Ab deposition did not require chemical modification to the capture molecule, terminating the DNA probe with an amine or thiol group improved both methods of detection, possibly by promoting the formation of covalent bonds between the DNA probe and nucleophilic centers in the Ppy. Nevertheless, ECD was ten times more sensitive than fluorescence detection, which appears to be the result of fluorescence quenching by the Ppy. Fluorescent signals were improved by extending the capture probe using a T-linker and by heating the array to 95° C. for 1 h prior to hybridization. Heating improved the fluorescence signal and reduced the ECD signal, indicating that it was affecting the Ppy rather than the immobilized DNA probes, possibly by reducing the conductivity of the former. Pretreatment of Ppy with propanolamine had the opposite effect—the ECD signal improved while the fluorescence signal decreased. Comparing the hybridization signals using probes that were synthesized situ versus those immobilized on Ppy, we observed higher fluorescence signals from the latter. While differences appear to be related to the proximity of the fluorescent dye to the quenching effect of the Pt electrode or the Ppy, there are other factors that could influence these results as well. The versatility of the 12K microarray to support different methods for depositing capture elements (DNA and Ab) and different methods for detecting target binding creates opportunities for developing multiplex assays that use orthogonal methods to identifying desired target molecules including but not limited to protein, peptides, organisms, and nucleic acid biomarkers.

Two methods were used for immobilizing DNA probes on individual electrodes. The first method involved in situ synthesis using the CombiMatrix commercial process. The second method involved deposition of Ppy and DNA probes using the same procedure described previously for Ab immobilization. In short, a chip map was created for the PotentioSense and MX300 instruments by designating through the software which electrodes were to be addressed, the current to be applied, and the time of application. The map created four replicated areas on the array that corresponded to the four chambers of a plastic hyb cap (ElectraSense Hybridization Cap, 4×2 K, CombiMatrix Corp., Mukilteo, Wash.). Within each area, 2×2 blocks of electrodes were connected through CMOS transistor switches on the array so that they received the same current for the same period of time. To prevent non-specific binding, the array was treated with PBSC for 5 min, washed three times with PBS containing 0.1% Tween 20 (PBST), three times with PBS, and three times with 0.1 M dibasic sodium sulfate prior to adding pyrrole for electrodeposition. After Ppy deposition, the array was washed twice with PBS; and the DNA oligonucleotide, diluted in PBS, was added for 15 min at 25° C. The array was washed three times with PBSC and blocked with the same for 2-5 min. For deposition of a second oligonucleotide, the array was washed thrice with PBST, with PBS and with sodium sulfate prior to Ppy deposition as described above. After probe deposition, the microarray was blocked with PBSC for 1 h, and stored at 4° C. To inhibit thiol-DNA immobilization, Ppy was deposited as described, and the array was washed twice with PBS and incubated for 15 min at 25° C. in the dark with a blocking solution. The array was washed three times with PBS, and the thiol-DNA was deposited in the prescribed manner.

Microarray Hybridization

Hybridizations were done manually so that results from experiments using ECD and fluorescence detection were processed in the same manner. The microarray was fitted with a four-chamber hyb cap and washed with PBSC before adding a dilution of biotinylated DNA target in 2×PBST or 2×PBST alone (control). Following a 1 h incubation at 50° C., the chambers were washed three times with 2×PBST, the four-chambered hyb cap was removed and replaced with a single-chambered hyb cap, and the array was washed three more times. The array was incubated with 5×PBSC (BioFX, Owings Mills, Md.) for 20 min at 25° C. and washed three times with 2×PBST. For fluorescence detection, microarrays were incubated for 30 min with Cy5-streptavidin (GE Healthcare, Amersham Biosciences, Piscataway, N.J. diluted to 1.0 µg/mL in 2×PBST. Arrays were washed five times in PBSC, twice in PBS, and scanned on a GenePix 4000B (Axon Instruments, Molecular Devices, Sunnyvale, Calif.). For ECD, microarrays were incubated for 30 min with Poly-80-HRP Streptavidin (Fitzgerald Industries International, Acton, Mass.) diluted 1:1,000 in PBST. Arrays were washed four times with PBSC, once with PBS, and twice with pH 4 Conductivity Buffer Substrate (BioFX). TMB Conductivity 1 Component HRP Microwell Substrate (BioFX) was added to the array, and it was scanned immediately with an ElectraSense microarray reader (CombiMatrix Corp.). Data were quantified using Microarray Imager or ElectraSense software (CombiMatrix Corp.) for fluorescent scans or ECD respectively.

Figure 19:
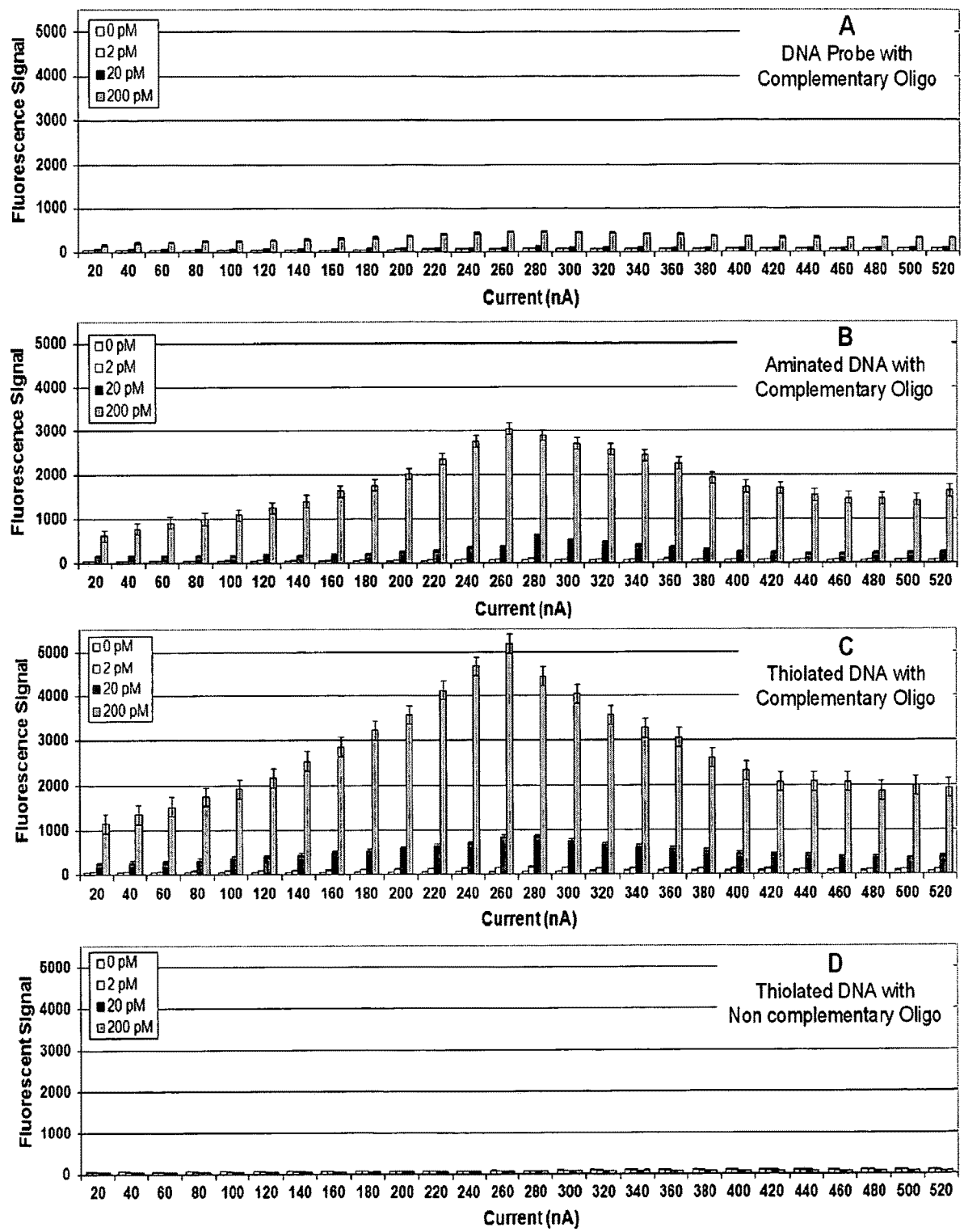
FIG. 19. (A) Fluorescence detection of target oligonucleotide binding to a complementary probe immobilized on Ppy deposited using constant current from 10 to 520 nA for 1.0 sec. Different concentrations (0, 2, 20 or 200 pM) of target oligonucleotide were incubated in individual chambers of a four-chamber hyb cap, and binding was detected using Cy5-SA. (B) Same as (A), but a 5'-aminated complementary probe was immobilized on the Ppy. (C) Same as (A) but a 5'-thiolated complementary probe was immobilized on the Ppy. (D) Same as (A) but a 5'-thiolated non-complementary probe was immobilized on the Ppy.
Figure 20:
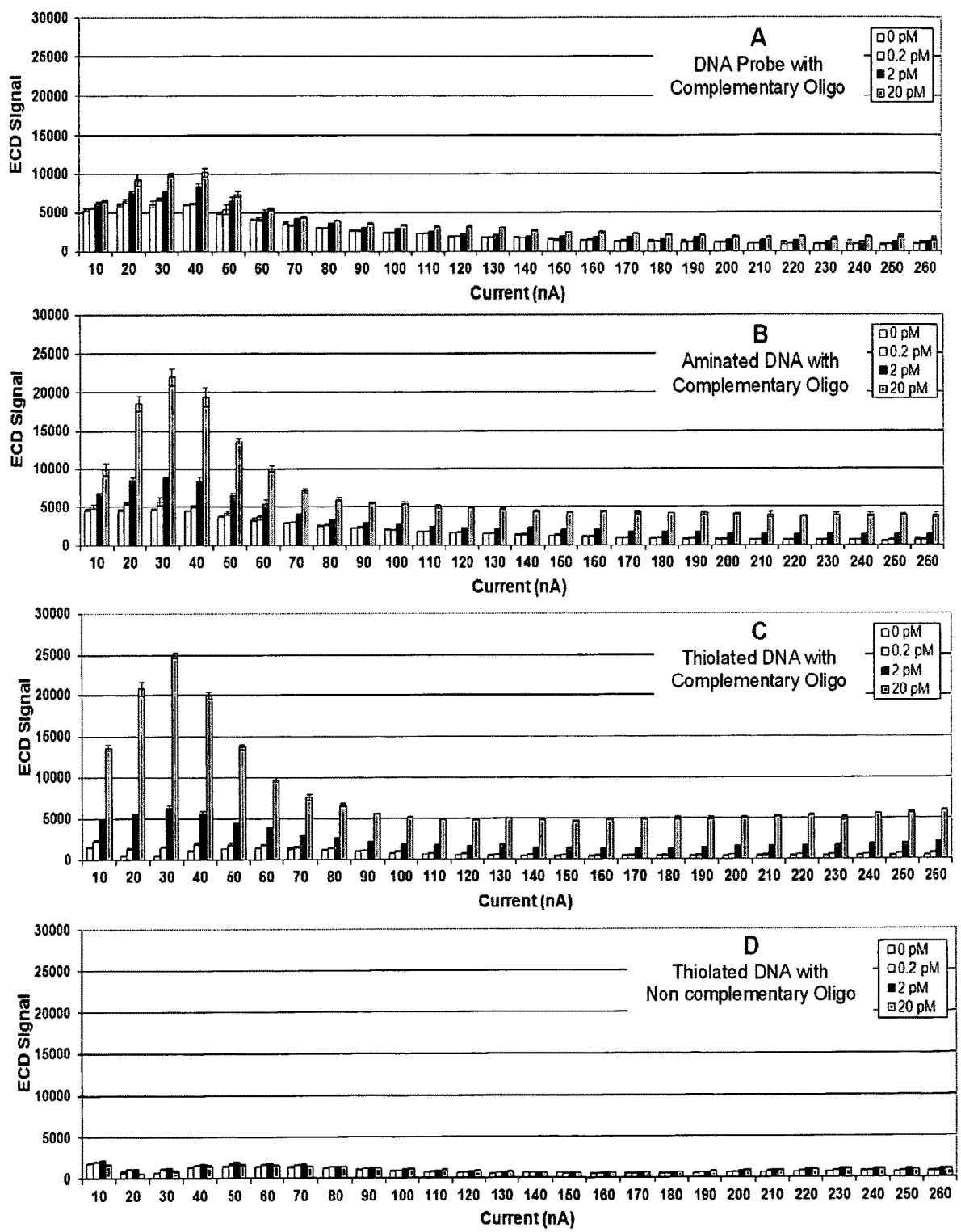
FIG. 20. (A) Electrochemical detection of target oligonucleotide binding to a complementary DNA probe immobilized on Ppy deposited using constant current from 10 to 260 nA for 1.0 sec. Different concentrations (0.0, 0.2, 2.0 or 20.0 pM) of target oligonucleotide were incubated in individual chambers of a four-chamber hyb cap, and binding was detected using HRP-SA. (B) Same as (2A), but a 5'-aminated complementary probe was immobilized onto the Ppy. (C) Same as (2A) but a 5'-thiolated complementary probe was immobilized on the Ppy. (D) Same as (2A) but a 5'-thiolated non-complementary probe was immobilized on the Ppy.

Ppy deposition conditions (current and time) influence assay results, and the conditions that favor optimum ECD are different than those that favor optimum fluorescence detection. For studying DNA immobilization on Ppy, the same assay protocols and variables were studied and adjusted as with the immunoassays; changes were made to optimize detection of DNA hybridization. FIG. 19A illustrates the results from fluorescence detection of DNA hybridization to a complementary, unmodified DNA probe (i.e., no 5' terminal modification) fixed onto the surface of the Ppy. Considering the maximum amount of target oligonucleotide (200 pM) used in the assay, the hybridization signals were low with the optimum signals on Ppy deposited at 260 nA for 1 sec. FIG. 19B illustrates the results from target hybridization to a complementary probe with a 5'-terminal amine. Compared with the unmodified DNA, the aminated DNA probe produced almost eight times the signal. A greater than ten-fold increase was obtained when a complementary thiol-DNA probe was used (FIG. 19C). The negative control using a thiolated non complementary probe (FIG. 19D) produced a negligible background hybridization signal.

This experiment was repeated using ECD, and FIG. 20A-D illustrate the results. As observed using fluorescence detection, aminated and thiolated probes produced much higher hybridization signals (2-2.5 times) than unmodified DNA. However, for ECD, maximum hybridization signals were observed using Ppy deposited at 30 nA; and very high ECD signals were obtained using one tenth the concentration of labeled target.

These results raised two issues—the importance of terminal groups on DNA for binding to Ppy and the relationship between conductivity and fluorescence quenching. To determine whether or not the binding of the thiolated DNA probes is mediated through the covalent bond formation, microarrays with electropolymerized Ppy were incubated for 15 min at room temperature with either PBS, or 1.0 M propanolamine, 1.0 M cysteine, or 1.0 M thioglycolic acid in PBS, after which 5'-thiolated complementary DNA was deposited as usual. Hybridization was measured using 200 pM or 20 pM DNA target and fluorescence detection or ECD respectively.

Figure 21:
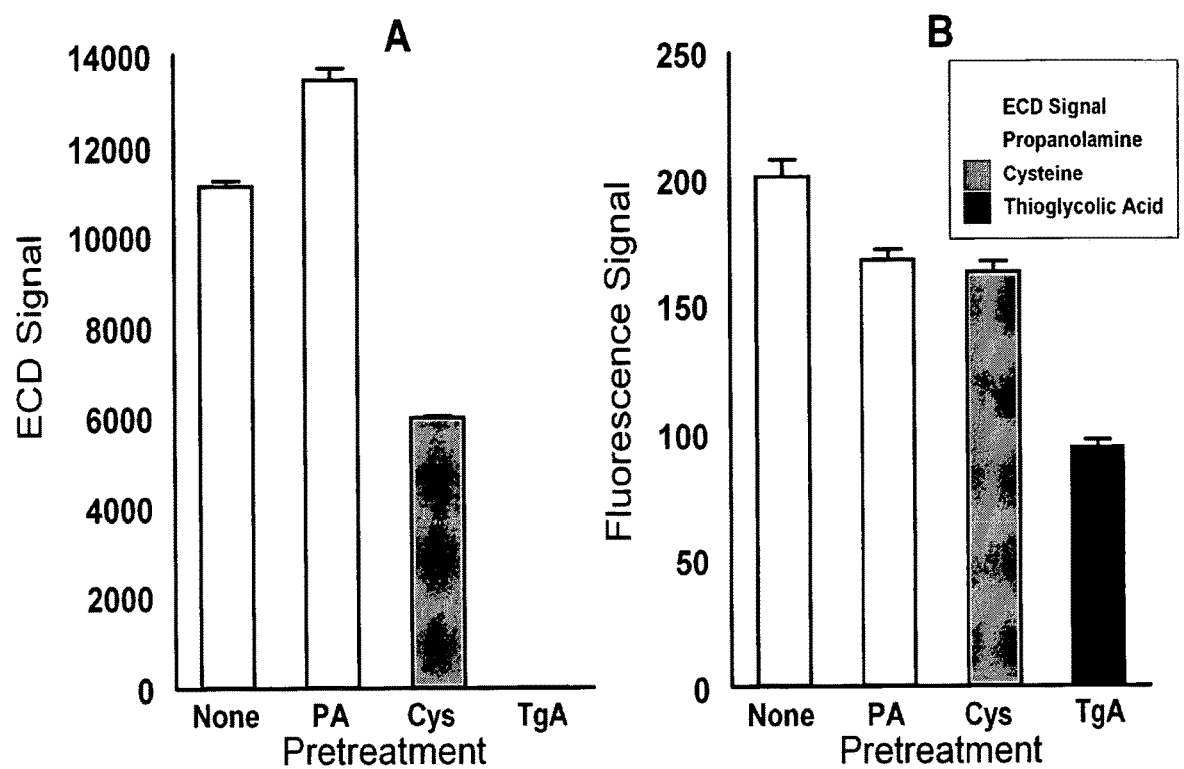
FIG. 21. Inhibition of hybridization signals by Ppy pretreatment with 1.0 M propanolamine, cysteine, or thioglycolic acid prior to immobilization of thiolated DNA. (A) Effect on ECD measured on electrodes with Ppy polymerized at 40 nA following hybridization with 20 pM 5'-biotinylated complementary oligonucleotide. (B) Effect on fluorescence detection, measured on electrodes with Ppy polymerized at 260 nA and hybridized with 200 pM of complementary oligonucleotides.

FIG. 21 shows that cysteine and thioglycolic acid reduced both fluorescence and ECD signals with the latter demonstrating excellent effectiveness in both assays. Pretreatment of the Ppy with propanolamine had mixed effects on the assay by increasing the signal as measured by ECD while decreasing the signal as measured by fluorescence. Without being bound by theory, this result suggests that propanolamine affected some quality of the Ppy (e.g., conductivity) that may not be related to blocking oligonucleotide binding. The apparent inverse relationship between Ppy conductivity and fluorescence quenching was not observed with the immunoassay on the array.

In an embodiment, a charge value of 250 nC is reached using constant current for Ppy electropolymerization on the 43μ Pt electrodes (260 nA for 1 sec) of the microarray.

Figure 22:
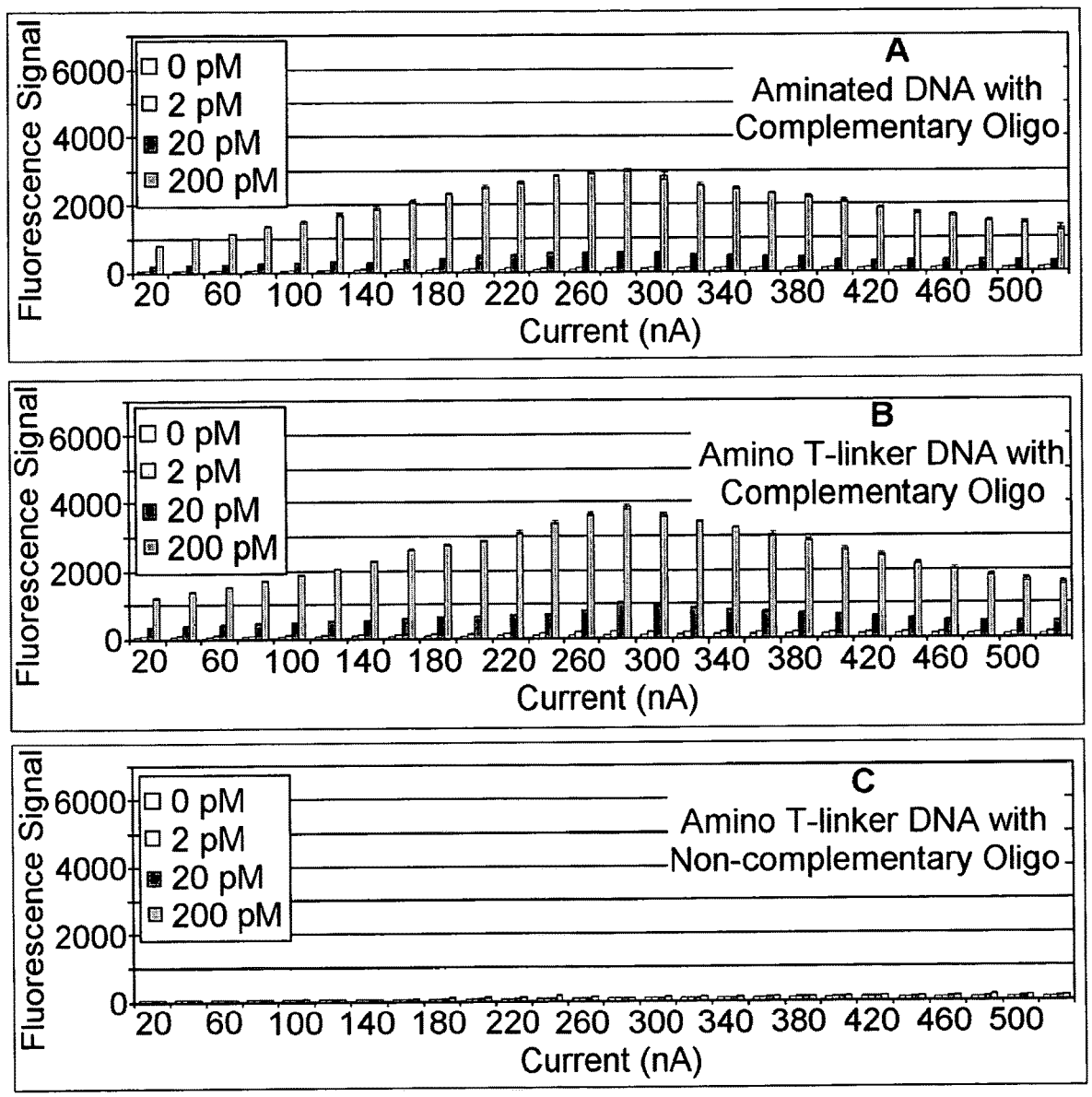
FIG. 22. (A) Fluorescence detection of target oligonucleotide binding to a complementary aminated DNA probe immobilized on Ppy deposited using constant current from 10 to 520 nA for 1.0 sec. Different concentrations (0, 2, 20, or 200 pM) of 5'-biotinylated target oligonucleotide were incubated in individual chambers of a four-chamber hyb cap, and binding was detected using Cy5-SA. (B) Same as (3A), but a complementary DNA probe with a 5'-aminated T-linker was immobilized on the Ppy. (C) Same as (3A), but a non-complementary DNA probe with an aminated T-linker was immobilized on the Ppy.

To determine if extending the probe further from the surface of the Ppy would change the fluorescence signal, we added a 20 T-linker (SEQ ID NO:4) between the 5'-end and the terminal amine (aminated T-linker). FIG. 22 illustrates that the probe with the aminated T-linker showed a 33% increase in fluorescence hybridization signals compared to signals obtained using the aminated DNA probe without the linker.

Figure 23:
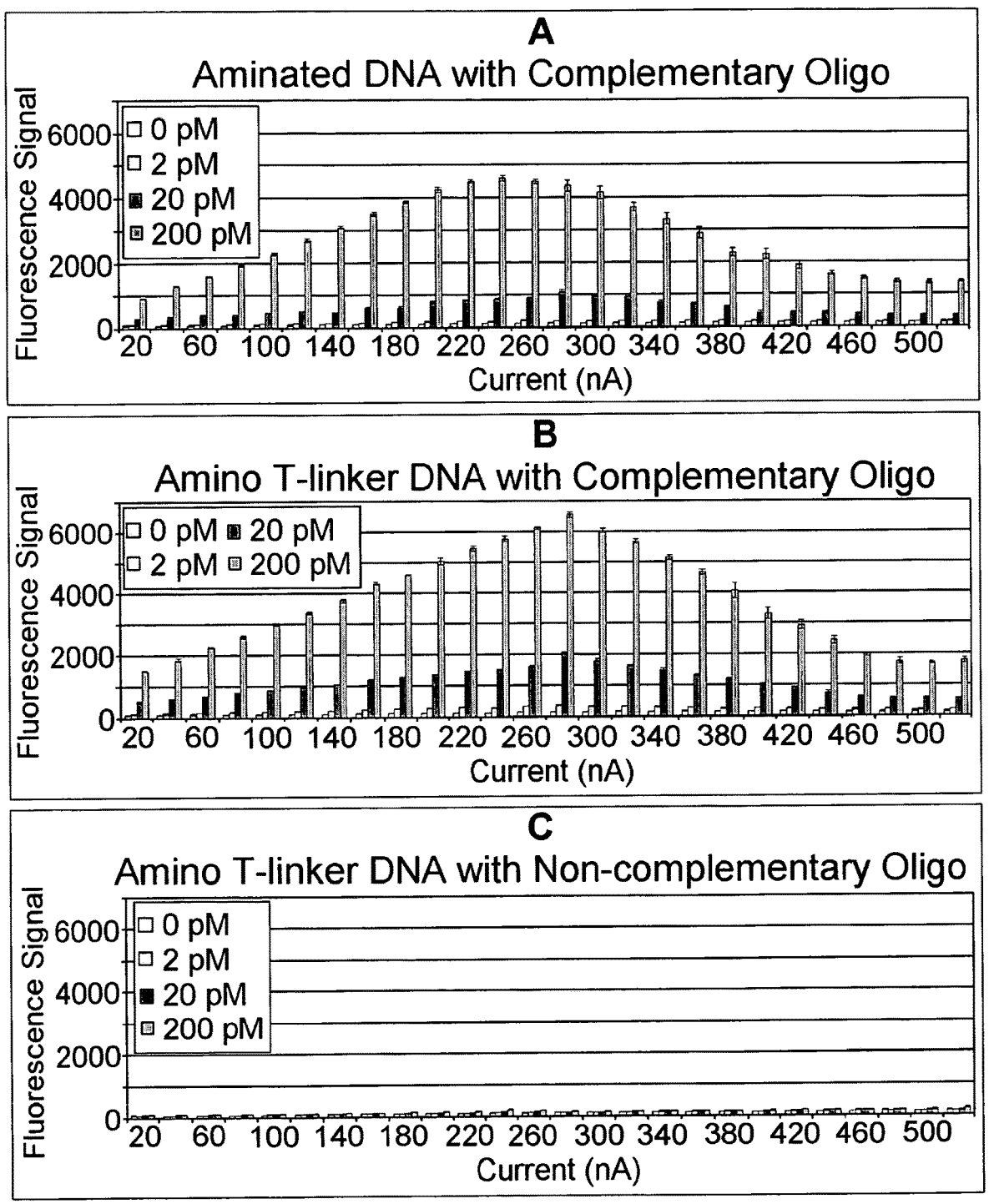
FIG. 23. Fluorescence detection of rehybridization by target oligonucleotide to probes on the microarray used in FIG. 21 following stripping at 95° C. for 1 h. Different concentrations (0, 2, 20, or 200 pM) of biotinylated target oligonucleotide were incubated in individual chambers of a four-chamber hyb cap, and binding was detected using Cy5-SA. (A) Complementary 5'-aminated DNA probe immobilized on Ppy deposited using constant current from 10 to 520 nA for 1.0 sec. (B) Same as (4A), but a complementary DNA probe with an 5'-aminated T-linker was immobilized on the Ppy. (C) Same as (4A), but a non-complementary DNA probe with a 5'-aminated T-linker was immobilized on the Ppy.

In an embodiment, the microarrays were stripped for reuse by incubating them in PBS at 95° C. for 1 h. FIG. 23A-C illustrates the fluorescence signals obtained after stripping the microarray that was used for studies reported in FIG. 22 and rehybridizing it with 5'-biotinylated oligonucleotide. Stripping, removed all fluorescence, and it could not be reconstituted by labeling with Cy5-SA alone (data not shown). However, upon rehybridization and labeling, the fluorescence signals were 50 to 70% higher than in the original hybridization. To ensure that this enhancement was not related to hybridization and stripping, a microarray was heated with immobilized probes to 95° C. for 1 h prior to hybridization and obtained comparable results (data not shown). Moreover, stripping or preheating the microarrays had negligible effect on hybridization to the non-complementary DNA probes (FIG. 23C).

Figure 24:
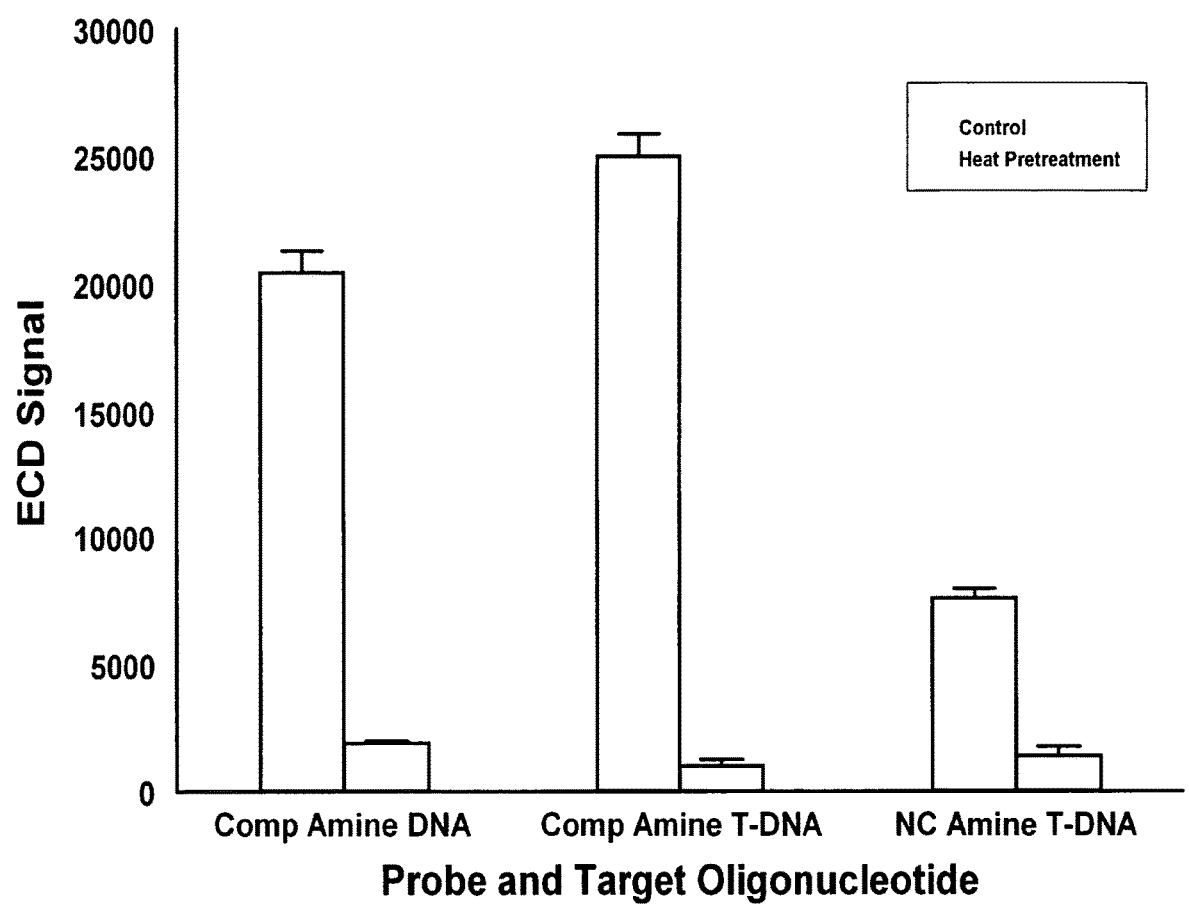
FIG. 24. Effects on ECD of adding a 5'-aminated 20 T-linker to DNA probes and preheating the immobilized probes prior to hybridization. Polypyrrole was deposited at 30 nA, and 20 pM of biotinylated oligonucleotide was hybridized on the array. A second microarray was incubated in 2×PBST for 1 h at 95° C. and washed once in PBS prior to hybridization.

These studies were repeated using ECD and FIG. 24 shows that adding an aminated T linker to the DNA probe increased hybridization signals by 22%; however, heating the microarray prior to hybridization reduced the ECD signal to background levels. The opposite effects of heating on fluorescence detection and ECD suggest that heating may be changing the nature of the Ppy as opposed to altering the DNA probes. Without being bound by theory, reduced conductivity would reduce ECD signals while improving fluorescence signals by reducing quenching—a function of conductivity.

Figure 25:
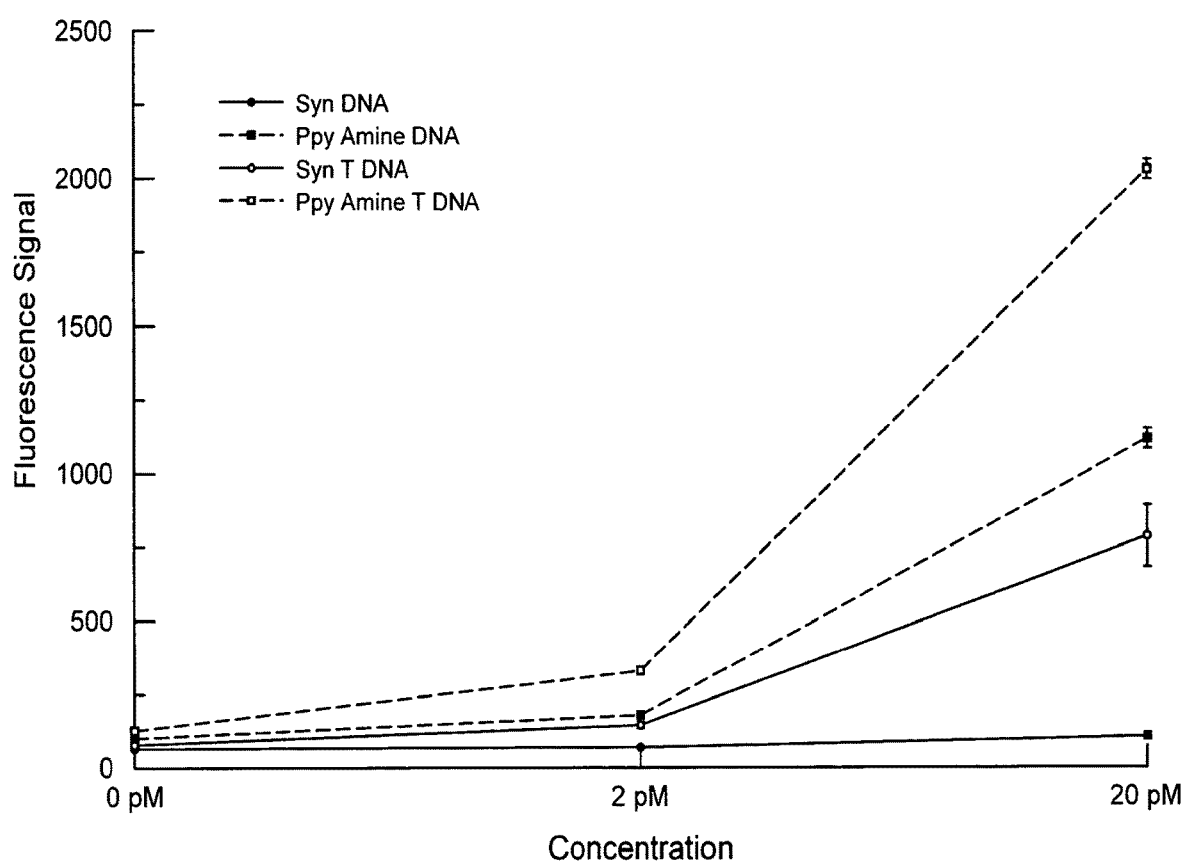
FIG. 25. Concentration of target versus signal intensity plot for two microarrays containing complementary and non complementary DNA probes either synthesized (Syn) in situ or immobilized on polypyrrole (Ppy). The data illustrate results using a synthesized complementary DNA probe (Syn DNA), a synthesized complementary DNA probe with a 3' 20 T-linker (Syn T DNA) (SEQ ID NO:4), a complementary 5' aminated DNA probe on Ppy (Ppy Amine DNA), and a complementary DNA probe with a 5' aminated T-linker (Ppy Amine T DNA). Microarrays were hybridized with 0, 2, or 20 pM of biotinylated oligonucleotide.
Figure 26:
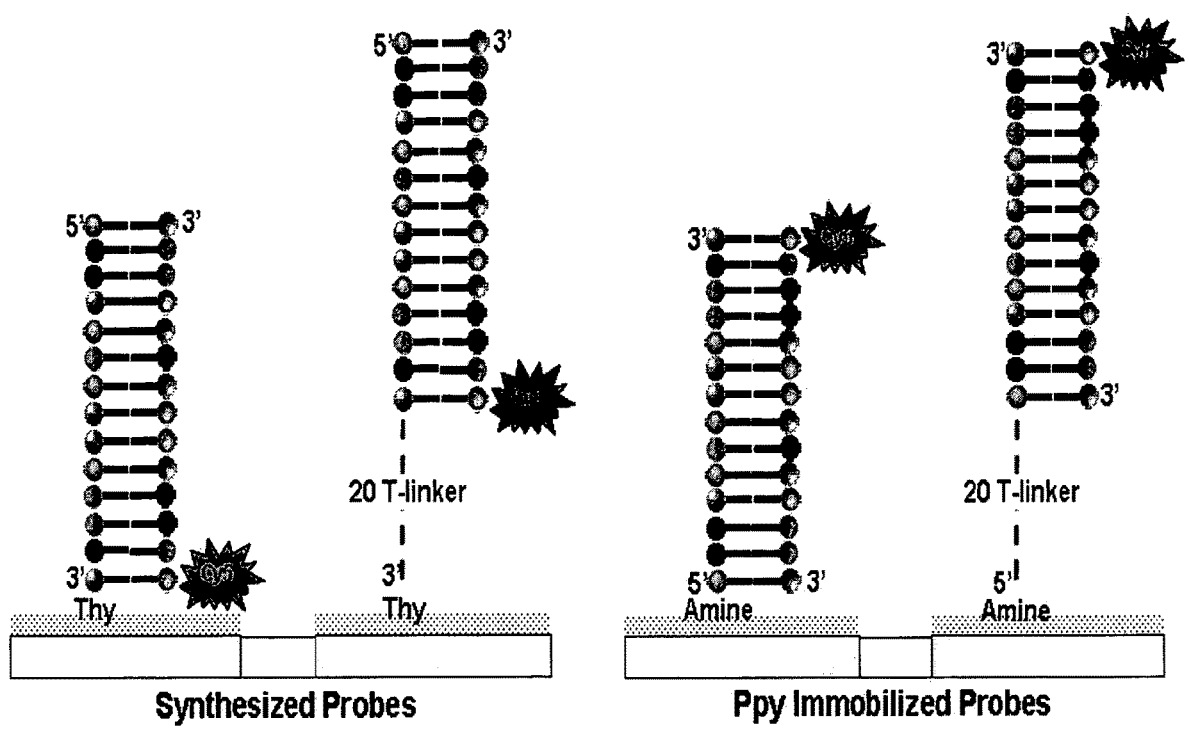
FIG. 26. Illustration of the relationship between the Cy5 dye on the target oligonucleotide and the Pt or Ppy surface on the electrode for the DNA capture probes either synthesized in situ or immobilized using Ppy respectively.

Because oligonucleotides can be synthesized on the microarray, an array was made via synthesis and contained probes with and without 20-T linkers and in the same configuration as the Ppy arrays. FIG. 25 compares results from a synthesized microarray against one prepared using Ppy that was pretreated with heat to obtain maximum hybridization signals. The highest hybridization signals were obtained using the complementary probe with aminated T-linker on Ppy, followed by the aminated DNA probe on Ppy and the synthesized DNA probe with a 20T-linker. The lowest hybridization signals were obtained with the synthesized DNA probe. While these differences may be due to a number of factors, the data suggest an interesting correlation between the intensities of the fluorescence signals and distances between the Cy5 and the quenching surface (Ppy or Pt). As illustrated in FIG. 26, in situ DNA synthesis occurs 3' to 5', which means that an oligonucleotide labeled on its 5'-end will hybridize with the Cy5 next to the Pt electrode. Adding a 20 T-linker (SEQ ID NO:4) will move the Cy5 away from the membrane by 20 bases. The aminated DNA is tethered to the Ppy by its 5'-end, and the target oligonucleotide hybridizes with the Cy5 in the opposite orientation and 21 bases away from the Ppy—about the same distance as synthesized DNA with a 20 T-linker. The aminated T-linker DNA adds another 20 bases on the 5'-end, which puts the Cy5 the furthest away (41 bases) from the Ppy. However, this model is predicated on a uniform lawn of DNA standing perpendicular to the surface. Other factors may also have a bearing on these results, e.g., differences in the surface densities of the DNA probes, steric hindrance of hybridization and/or labeling, and possibly DNA electroconductivity.

The invention claimed is:

1. A process of preparing two or more oligonucleotides on a microarray, comprising:
(a) electropolymerizing a monomer on one or more microelectrodes of a microarray using an electropolymerizing solution with one or more electropolymerizing parameters to form a first thickness on at least a first microelectrode and electropolymerizing the monomer with one or more different electropolymerizing parameters to form at least a second thickness on at least a second microelectrode, where the first microelectrode and the second microelectrode are selected from the one or more microelectrodes, where the first thickness is different than the second thickness, where the one or more electropolymerizing parameters are selected from the group consisting of potential, current and time of electropolymerizing;
(b) exposing the microarray to a first solution containing a first oligonucleotide for attachment to the first thickness on the one or more electrodes; and
(c) exposing the microarray to a second solution containing a second oligonucleotide for attachment to the second thickness on the one or more electrodes, where one or both the first thickness and the second thickness facilitates detection of one or both the first oligonucleotide and the second oligonucleotide.

2. The process of claim 1, further comprising applying a blocking protein prior to one or more of steps (a), (b) and (c).

3. The process of claim 2, further comprising washing the microarray to remove the blocking protein.

4. The process of claim 1, where step (a) further comprises washing the microarray to remove the electropolymerizing solution.

5. The process of claim 1, where step (b) further comprises washing the microarray to remove the first solution.

6. The process of claim 1, where the monomer is selected from the group consisting of pyrrole functionalized pyrrole and combinations thereof.

7. The process of claim 1, where the monomer is selected from the group consisting of thiophenol, aniline, phenylene sulfide, phenylenediamine, diaminohaphthalene, phenol, phenolic derivatives, and combinations thereof.

8. The process of claim 1, where the microarray is a CMOS device.

9. The process of claim 1, where the monomer is electropolymerized to a conducting polymer.

10. The process of claim 1, where the monomer is electropolymerized to a non conducting polymer.

11. A process of preparing a multiplex microarray of serially attached different oligonucleotides on a microarray, comprising:
(a) electropolymerizing a monomer on one or more microelectrodes of the microarray using an electropolymerizing solution with one or more electropolymerizing parameters to form a first thickness on a first microelectrode and electropolymerizing the monomer with one or more different electropolymerizing parameters to form at least a second thickness on a second microelectrode, where the first microelectrode and the second microelectrode are selected from the one or more microelectrodes, where the first thickness is different than the second thickness, where the one or more electropolymerizing parameters are selected from the group consisting of potential, current and time of electropolymerizing, where the electropolymerizing solution containing the monomer does not contain any oligonucleotides;

(b) exposing the microarray with a first oligonucleotide solution containing a first oligonucleotide for attachment to the first thickness on the first microelectrode; and (c) exposing the microarray to a second oligonucleotide solution containing a second oligonucleotide for attachment to the second thickness on the second microelectrode, where one or both the first thickness and the second thickness facilitates detection of one or both the first oligonucleotide and the second oligonucleotide.

12. The process of claim 11, further comprising applying a blocking protein prior to one or more of steps (a), (b) and (c).

13. The process of claim 12, further comprising washing the microarray to remove the blocking protein.

14. The process of claim 11, where step (a) further comprises washing the microarray to remove the electropolymerizing solution.

15. The process of claim 11, where step (b) further comprises washing the microarray to remove the first oligonucleotide solution.

16. The process of claim 11, where the monomer is selected from the group consisting of pyrrole, functionalized pyrrole and combinations thereof.

17. The process of claim 11, where the monomer is selected from the group consisting of thiophenol, aniline, phenylene sulfide, phenylenediamine, diaminohaphthalene, phenol, phenolic derivatives, and combinations thereof.

18. The process of claim 11, where the microarray is a CMOS device.

19. The process of claim 11, where the monomer is electropolymerized to a conducting polymer.

20. The process of claim 11, where the monomer is electropolymerized to a non conducting polymer.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: residue modified with biotin

```
<400> SEQUENCE: 1
tgcttctgta cgttgtaccc a                                      21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
tgggtacaac gtacagaagc a                                      21

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
caatagctcc tgctacaaat gc                                     22

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
tttttttttt tttttttttt                                        20
```